(12) United States Patent
Wang et al.

(10) Patent No.: US 12,233,182 B2
(45) Date of Patent: Feb. 25, 2025

(54) INSTANT UNDERWATER BIO-ADHESIVE CONTAINING CATECHOL MOIETIES AND WATER-RESISTANT CHOLESTEROL

(71) Applicant: City University of Hong Kong, Kowloon (HK)

(72) Inventors: Dong-An Wang, Kowloon (HK); Chao Tao, Zibo (CN); Min Jin, Anqing (CN)

(73) Assignee: City University of Hong Kong, Kowloon (HK)

( * ) Notice: Subject to any disclaimer, the term of this patent is extended or adjusted under 35 U.S.C. 154(b) by 114 days.

(21) Appl. No.: 17/959,091

(22) Filed: Oct. 3, 2022

(65) Prior Publication Data

US 2024/0108782 A1   Apr. 4, 2024

(51) Int. Cl.
*A61L 24/08*    (2006.01)

(52) U.S. Cl.
CPC ......... *A61L 24/08* (2013.01); *A61L 2300/232* (2013.01)

(58) Field of Classification Search
None
See application file for complete search history.

(56) References Cited

U.S. PATENT DOCUMENTS 10,568,984 B2    2/2020  Wang et al.
11,155,568 B2 *  10/2021 Helle ................. C04B 24/18

OTHER PUBLICATIONS

Cui et al. (APL Materials 5(11), 116102 (2017).*
Zhu et al., "A DOPA-Functionalized Chondroitin Sulfate-Based Adhesive Hydrogel as a Promising Multi-functional Bioadhesive", Journal of Materials Chemistry-B, 7 (2019) 10: 1741-1752.
Tao et al., "Dopamine based adhesive nanocoatings on extracellular matrix (ECM) based grafts for enhanced host-graft interfacing affinity", Nanoscale, 13 (2021): 18148-18159.
Zhu et al., "A novel DOPA-albumin based tissue adhesive for internal medical applications", Biomaterials, 147 (2017): 99-115.
Fan et al., "A mussel-inspired doublecrosslink tissue adhesive for internal medical use", Acta Biomaterialia, 33 (2016): 51-63.

\* cited by examiner

*Primary Examiner* — Shirley V Gembeh
(74) *Attorney, Agent, or Firm* — Norton Rose Fulbright US LLP

(57) ABSTRACT

A novel bio-adhesive suitable for in vivo and/or underwater medical use is disclosed. The bio-adhesive includes base polymers conjugated to hydrophobic moieties for imparting water-resistance and/or to phenolic moieties for enhancing adhesion to biological tissues. The bio-adhesive exhibits low toxicity and is highly compatible with biological tissues.

18 Claims, 13 Drawing Sheets

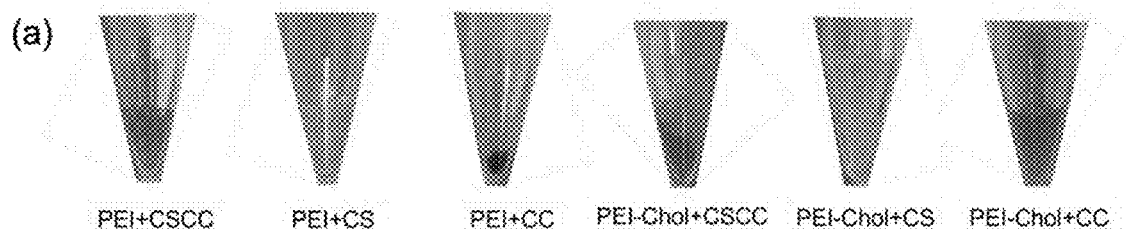
FIG. 3A
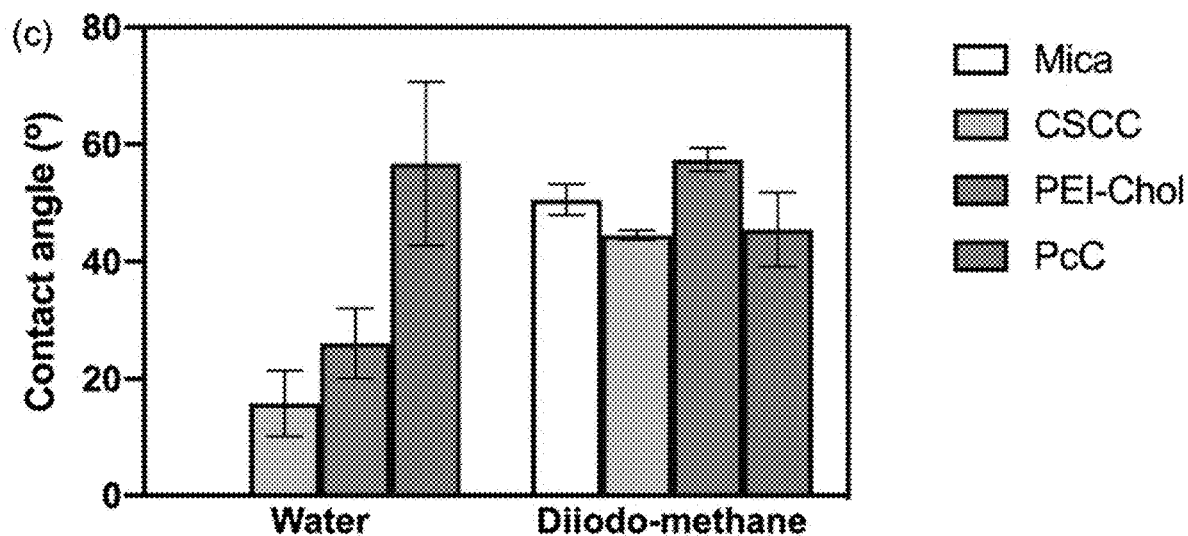
FIG. 3B
FIG. 3C

INSTANT UNDERWATER BIO-ADHESIVE CONTAINING CATECHOL MOIETIES AND WATER-RESISTANT CHOLESTEROL

TECHNICAL FIELD

This invention relates to the field of chemistry and adhesives for medical applications.

BACKGROUND OF THE INVENTION

Bio-adhesives that exhibit high adhesive strength, ease of use, and biocompatibility currently can serve as alternatives to sutures or staples in many clinical applications. For example, medical procedures involving integration of implanted grafts with tissues, wound closure, hemostasis, and to prolong the duration of administration at a site can employ bio-adhesives as alternatives to sutures or staples (Chen et al., Zhang et al.). Commercially-available bio-adhesives can be categorized into natural material-derived bio-adhesives, such as fibrin glues based on clotting (e.g., TISSEEL®), and synthetic material-derived bio-adhesives such as polycyanoacrylates (e.g., HISTOACRYL®) (Li et al., Duan et al., Mehdizadeh et al.). Although TISSEEL® has been proven to be more efficient and safer as an adjunct to hemostasis (Li et al.), its limitations and potential risks should not be overlooked. For example, blood-borne cross-infection may result from the human plasma source of TISSEEL® (Li et al., Hino et al., Horowitz et al.).

Synthetic polymer-derived bio-adhesives typically exhibit high adhesion with tissues due to their good mechanical strength. However, they can cause significant damage to tissues after detachment. Additionally, chronic inflammation may be caused by the release of degradation products of the synthetic polymer-derived bio-adhesives (Ma et al., Ge et al.). Many synthetic polymer-derived bio-adhesives are non-biodegradable and present relatively poor biocompatibility (Farrar et al., Cedano et al.). For hard tissues, e.g., cartilage with a lubricated and flat surface, synthetic polymer-derived bio-adhesives in liquid form are difficult to treat topically. Therefore, diffusible synthetic liquid polymer bio-adhesives with high adhesive strength are not easy to use and may carry biosafety risks when applied to surgeries on hard tissues.

In addition to poor biocompatibility, many commercial bio-adhesives exhibit poor adhesion under wet conditions (Ge et al., Yuk et al.). Many commercial bio-adhesives are prone to swelling in humid environments, leading to hydrated forms with low mechanical strength. The reduced mechanical strength can disrupt the cohesion, which can lead to undesirable detachment or even failure in surgeries in clinical use. Therefore, there is a need for biocompatible bio-adhesives that maintain high adhesive strength upon exposure to water and high-humidity conditions.

BRIEF SUMMARY OF THE INVENTION

The poor adhesive strength of bio-adhesives exposed to water is often caused by their hydrated forms. Disclosed herein are bio-adhesives with increased hydrophobicity that have enhanced adhesive strength under wet conditions and increased biocompatibility. The bio-adhesives may in some instances contain a hydrophobic moiety that can impart water-resistance to the bio-adhesives and that are endogenous to the human body. The hydrophobic moiety can increase adhesive biocompatibility and effectiveness in wet or moist environments. In some instances the hydrophobic moiety is covalently bound to a polycationic polymer. In some aspects, the bio-adhesives contain a phenolic moiety. The phenolic moiety can increase the adhesiveness of the bio-adhesive. In some instances, the phenolic moiety is covalently bound to a polyanionic polymer.

The bio-adhesives may be used as biomedical adhesive that may include underwater and medical applications. Not to be bound by theory, but the bio-adhesive's mechanism of action is believed to be based on electrostatic interactions between positively-charged polymer and negatively-charged polymer, such as a negatively-charged polysaccharide. The bio-adhesives in some instances, may include a cholesterol ester moiety for enhanced water-resistance and a catechol moiety for more robust adhesion to surrounding tissues. In some embodiments, the cohesion may be provided by electrostatic interactions between the polyanion and the polycation, the water-resistance is bolstered by the inclusion of a cholesterol group, and/or the catechol moiety enhances adhesion to substrates.

The bio-adhesives disclosed herein can be prepared relatively rapidly, e.g., in a few seconds, thereby making the bio-adhesives expedient for medical applications. In vitro mechanical measurements demonstrated that the novel bio-adhesives disclosed herein exhibit superior underwater adhesion performance as compared to the commercially-available fibrin sealant TISSEEL®. Animal experiments in a rat mastectomy model and a rat cartilage graft implantation model demonstrated the potential for use of the bio-adhesive in various medical applications, including closing surgical incisions, reducing the formation of seroma, and adhering tissue engineering grafts.

Some aspects of the disclosure are therefore directed to a bio-adhesive comprising a polycationic polymer functionalized with a hydrophobic moiety and a polyanionic polymer. In some aspects, the functionalized polycationic polymer comprises a polycationic polymer having a hydrophobic moiety. The hydrophobic moiety may help impart water-resistance to the bio-adhesive. The polycationic polymer may be polyethyleneimine, chitosan, poly dimethyl diallyl ammonium chloride (PDADMAC), polyamidoamine-epichlorohydrin (PAE), or any polymer that includes a primary and/or secondary amine and/or tertiary amine moiety. In some aspects, the hydrophobic moiety is a cholesterol, stearic acid, oleic acid, lecithin, sulfonate, or a quaternary ammonium salt moiety or a combination thereof that is conjugated to the polycationic polymer. The amount of hydrophobic moieties conjugated to the polycationic polymer can be varied to adjust the water-resistance of the bio-adhesive. The polyanionic polymer can be a negatively-charged polysaccharide. Non-limiting examples of negatively-charged polysaccharides include chondroitin sulfate, glycosaminoglycan, carrageenan, gum Arabic, alginate, xanthan, guar gum, pectin, sodium alginate, hyaluronic acid, gellan gum, heparin, and combinations thereof. In some aspects, the polyanionic polymer is conjugated to a phenolic moiety. The phenolic moiety can comprise catechol, catechin, dopamine, levopamine, epicatechin, or any compound that includes an aromatic ring and at least two hydroxyl groups. The amount of phenolic moieties conjugated to the polyanionic polymer can be varied to adjust the adhesiveness of the bio-adhesive.

In some aspects, the bio-adhesive comprises from 15 to 60% by weight, based on a total weight of the bio-adhesive, of the functionalized polycationic polymer. The bio-adhesive can include an amount of functionalized polycationic polymer that is any one of, less than, greater than, or between 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 wt. %, or any range derivable therein. In some aspects, the bio-adhesive comprises from 40 to 85% by weight, based on a total weight of the bio-adhesive, of the polyanionic polymer. The bio-adhesive can include an amount of polyanionic polymer that is any one of, less than, greater than, or between 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, or 85 wt. %, or any range derivable therein.

In some aspects, the ratio of hydrophobic moieties conjugated to the polycationic polymer may be 4 hydrophobic moieties to each subunit of the polycationic polymer (4:1) to 1 hydrophobic moiety to 15 subunits of the polycationic polymer (1:15). For example, in some instances, there are an average of 1 cholesterol moiety to 2 ethyleneimine subunits of polyethyleneimine (1:2). In some instances, the ratio of hydrophobic moieties conjugated to the polycationic polymer may be any one of, less than, greater than, or between 4:1, 3:1, 2:1, 3:2, 1:1, 2:3, 1:2, 1:3, 1:4, 1:5, 1:6, 1:7, 1:8, 1:9, 1:10, 1:11, 1:12, 1:13, 1:14, 1:15, or any range derivable therein. In some aspects, the ratio of phenolic moieties conjugated to the polyanionic polymer may be 4 phenolic moieties to each subunit of the polyanionic polymer (4:1) to 1 phenolic moiety to 15 subunits of the polyanionic polymer (1:15). For example, in some instances, there are an average of 1 catechin moiety to 2 of the subunits of chondroitin sulfate comprising a D-glucuronic acid (GlcA) and N-acetyl-D-galactosamine (GalNAc) pair (1:2). In some instances, the ratio of phenolic moieties conjugated to the polyanionic polymer may be any one of, less than, greater than, or between 4:1, 3:1, 2:1, 3:2, 1:1, 2:3, 1:2, 1:3, 1:4, 1:5, 1:6, 1:7, 1:8, 1:9, 1:10, 1:11, 1:12, 1:13, 1:14, 1:15, or any range derivable therein.

Some aspects of the disclosure are directed to a medical adhesive kit for adhering biological tissues comprising a bio-adhesive as disclosed herein. Some aspects of the disclosure are directed to a method of adhering biological tissue, wherein the method comprises applying a bio-adhesive as disclosed herein to a biological tissue and adhering the biological tissue to another biological tissue and/or another portion of the same biological tissue, such as surrounding tissues.

Some aspects of the disclosure are directed to a method for preparing a bio-adhesive comprising combining a polycationic polymer having a hydrophobic moiety with a polyanionic polymer comprising a phenolic moiety to form the bio-adhesive. In some instances, the bio-adhesive is formed in a solution. In some instances, the components of the bio-adhesive are combined in dry form capable of being stored until a liquid is introduced to form the bio-adhesive. In some aspects, the polycationic polymer comprises polyethyleneimine, chitosan, poly dimethyl diallyl ammonium chloride, polyamidoamine-epichlorohydrin, or a combination thereof. In some aspects, the hydrophobic moiety is a cholesterol, stearic acid, oleic acid, lecithin, sulfonate, or a quaternary ammonium salt moiety, or a combination thereof. In some aspects, the polyanionic polymer is a negatively-charged polysaccharide selected from the group consisting of chondroitin sulfate, glycosaminoglycan, carrageenan, gum Arabic, alginate, xanthan, guar gum, pectin, sodium alginate, hyaluronic acid, gellan gum, heparin, and combinations thereof. In some aspects, the phenolic moiety is selected from catechol, catechin, dopamine, levopamine, epicatechin, or a combination thereof. In some instances, the bio-adhesive prepared is any one of the bio-adhesives disclosed herein.

Some aspects of the disclosure are directed to a method of use for a bio-adhesive. The bio-adhesive can be used to adhere two surfaces by contacting the two surfaces with each other and the bio-adhesive. The surfaces can be from the same object or different objects. One or both of the surfaces may be a surface of a biological material. In some instances, the two surfaces are two surfaces of a wound, two surfaces of a skin, two surfaces of an organ, two surfaces of an organism, two surfaces of a medical device, or surfaces of two different objects, such as an organism and a medical device. In some instances one or both of the surfaces are a hard tissue, such as cartilage, bone, shell, claw, tooth, and/or nail. In some instances one or both of the surfaces are wet or underwater when the surface is contacted with the bio-adhesive. In some instances, one or both of the surfaces are hard tissue and wet or underwater when the surface is contacted with the bio-adhesive. One or both of the surfaces may be a surface of a non-biological material. In some instances, one or both of the surfaces are of a medical device. In some instances, the bio-adhesive used in the method is any one of the bio-adhesives disclosed herein.

Also disclosed are the following Aspects 1 to 21 of the present invention. Aspect 1 is a bio-adhesive comprising a polyanionic polymer and a polycationic polymer functionalized with a hydrophobic moiety. Aspect 2 is the bio-adhesive of aspect 1, wherein the polycationic polymer comprises polyethyleneimine, chitosan, diallyl ammonium chloride, polyamidoamine-epichlorohydrin, or a combination thereof. Aspect 3 is the bio-adhesive of any one of aspects 1 to 2, wherein the hydrophobic moiety comprises a cholesterol, stearic acid, oleic acid, lecithin, sulfonate, or a quaternary ammonium salt moiety, or a combination thereof. Aspect 4 is the bio-adhesive of claim 3, wherein the functionalized polycationic polymer comprises a plurality of cholesterol moieties. Aspect 5 is the bio-adhesive of any one of aspects 1 to 4, wherein the polyanionic polymer comprises a negatively-charged polysaccharide. Aspect 6 is the bio-adhesive of aspect 5, wherein the negatively-charged polysaccharide comprises chondroitin sulfate, glycosaminoglycan, carrageenan, gum Arabic, alginate, xanthan, guar gum, pectin, sodium alginate, hyaluronic acid, gellan gum, heparin, or a combination thereof. Aspect 7 is the bio-adhesive of any one of aspects 1 to 6, wherein the polyanionic polymer further comprises a phenolic moiety. Aspect 8 is the bio-adhesive of aspect 7, wherein the phenolic moiety comprises catechol, catechin, dopamine, levopamine, epicatechin, or a combination thereof. Aspect 9 is the bio-adhesive of any one of aspects 1 to 8, wherein the bio-adhesive comprises from 15 to 60% by weight, based on a total weight of the bio-adhesive, of the functionalized polycationic polymer. Aspect 10 is the bio-adhesive of any one of aspects 1 to 9, wherein the bio-adhesive comprises from 40 to 85% by weight, based on a total weight of the bio-adhesive, of the polyanionic polymer. Aspect 11 is a medical adhesive kit for adhering biological tissues comprising the bio-adhesive of any one of aspects 1 to 10. Aspect 12 is a method for preparing a bio-adhesive, the method comprising contacting a polycationic polymer having a hydrophobic moiety with a polyanionic polymer comprising a phenolic moiety. Aspect 13 is the method of claim 12, wherein contacting the polycationic polymer with the polyanionic polymer forms a solution. Aspect 14 is the method of aspect 13, wherein the polycationic polymer and/or the polyanionic polymer is comprised in a solution when contacted. Aspect 15 is the method of aspect 14, wherein the polycationic polymer and/or the polyanionic polymer comprised in the solution is at least partially solubilized in the solution comprising the polycationic polymer and/or the polyanionic polymer. Aspect 16 is the method of any one of aspects 12 to 15, wherein the polycationic polymer comprises polyethyleneimine, chitosan, diallyl ammonium chloride, polyamidoamine-epichlorohydrin, or a combination thereof. Aspect 17 is the method of any one of aspects 12 to 16, wherein the hydrophobic moiety comprises a cholesterol, stearic acid, oleic acid, lecithin, sulfonate, or a quaternary ammonium salt moiety, or a combination thereof. Aspect 18 is the method of any one of aspects 12 to 17, wherein the polyanionic polymer is a negatively-charged polysaccharide comprising chondroitin sulfate, glycosaminoglycan, carrageenan, gum Arabic, alginate, xanthan, guar gum, pectin, sodium alginate, hyaluronic acid, gellan gum, heparin, or a combination thereof. Aspect 19 is the method of any one of aspects 12 to 18, wherein the phenolic moiety comprises catechol, catechin, dopamine, levopamine, epicatechin, or a combination thereof. Aspect 20 is the method of any one of aspects 12 to 19, wherein the bio-adhesive is the bio-adhesive of any one of aspects 1 to 10. Aspect 21 is a method for adhering two surfaces, the method comprising contacting the bio-adhesive of any one of aspects 1 to 10 to a first surface to form a bio-adhesive coated surface and contacting the bio-adhesive coated surface with a second surface, wherein contacting the bio-adhesive coated surface with a second surface adheres the first and second surfaces. Aspect 22 is the method of aspect 21, wherein the first and/or second surface is a surface of a biological material. Aspect 23 is the method of any one of aspects 21 to 22, wherein the first and/or second surface is a surface of a cartilage, bone, shell, claw, tooth, or nail. Aspect 24 is the method of any one of aspects 21 to 23, wherein the first surface is wet when contacted with the bio-adhesive and/or the second surface is wet when contacted with the bio-adhesive coated surface. Aspect 25 is the method of any one of aspects 21 to 24, wherein the method further comprises contacting the adhered first and second surface with water.

Throughout this application, the term "about" is used to indicate that a value includes the inherent variation of error for the measurement or quantitation method.

The use of the word "a" or "an" when used in conjunction with the term "comprising" may mean "one," but it is also consistent with the meaning of "one or more," "at least one," and "one or more than one."

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The compositions and methods for their use can "comprise," "consist essentially of," or "consist of" any of the ingredients or steps disclosed throughout the specification. Compositions and methods "consisting essentially of" any of the ingredients or steps disclosed limits the scope of the claim to the specified materials or steps which do not materially affect the basic and novel characteristic of the claimed invention.

The phrase "pharmaceutically acceptable" includes compositions that do not produce an allergic or similar untoward reaction when administered to a human. Typically, such compositions are prepared either as topical compositions, liquid solutions or suspensions, solid forms suitable for solution in, or suspension in, liquid prior to use can also be prepared. Routes of administration can vary with the location and nature of the condition to be treated, and include, e.g., topical, inhalation, intradermal, transdermal, parenteral, intravenous, intramuscular, intranasal, subcutaneous, percutaneous, intratracheal, intraperitoneal, intratumoral, perfusion, lavage, direct injection, and oral administration and formulation.

The phrase "hydrophobic" includes molecules having an HLB value of 0 to less than 10, where the HLB value is defined as HLB=20*Mh/M where Mh is the molecular mass of the hydrophilic portion of the molecule and M is the molecular mass of the whole molecule.

It is contemplated that any embodiment discussed in this specification can be implemented with respect to any method or composition of the invention, and vice versa. Furthermore, compositions of the invention can be used to achieve methods of the invention.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1A is a diagram depicting the synthesis of polyethyleneimine-cholesterol (PEI-Chol). FIG. 1B is a $^1$H NMR spectra of polyethyleneimine (PEI) and PEI-Chol. FIG. 1C is a FTIR spectra of PEI, cholesterol (Chol), and PEI-Chol.

FIG. 2A is a diagram depicting the synthesis of catechin modified chondroitin sulfate (CSCC). FIG. 2B is a UV-vis spectra of chondroitin sulfate (CS), catechin (CC), and CSCC. FIG. 2C is a FTIR spectra of CS, catechin, and CSCC.

FIGS. 3A-3C. FIG. 3A is a series of photos of different combinations of CSCC, CS, PEI, CC, and PEI-Chol. FIG. 3B is a table describing products of different combinations of CSCC, CS, PEI, CC, and PEI-Chol. FIG. 3C is a graph depicting contact angles of water and diiodo-methane on mica coated without and with CSCC, PEI-Chol, and formed adhesive hydrogel (PcC).

FIG. 4A is a graph depicting dynamic light scattering (DLS) results of PEI-Chol (0.5 mg/mL). FIG. 4B is a graph depicting DLS results of CSCC (0.5 mg/mL). FIG. 4C is a graph depicting DLS results of PcC. FIG. 4D is a graph depicting zeta potential of PEI-Chol/CSCC mixture with different CSCC mass ratios.

FIG. 5A is a table identifying C, N, O, and S content of CSCC, PEI-Chol and PcC. FIG. 5B is a graph X-ray photoelectron spectroscopy (XPS) spectra depicting binding energies of CSCC, PEI-Chol, and PcC.

FIG. 7A is a schematic of the lap shear strength measurement between cartilage and dLhCG graft. FIG. 7B is a table depicting lap shear strength results of PcC bio-adhesive on cartilage treated under different conditions with Tissel as a control group.

FIG. 8A is a series of images of the surgical procedure of seroma. FIG. 8B is a graph depicting mean and total seroma volume of three groups collected at day 1, day 4, and day 7.

FIG. 10A is an image of rat articular cartilage. FIG. 10B is an image of a 2 mm diameter cylinder hole on cartilage. FIG. 10C is an image of dLhCG transplanted into the cartilage joint on day 1. FIG. 10D is an image of PcC/dLhCG transplanted into the cartilage joint on day 1.

DETAILED DESCRIPTION OF THE INVENTION

Figure 1A:
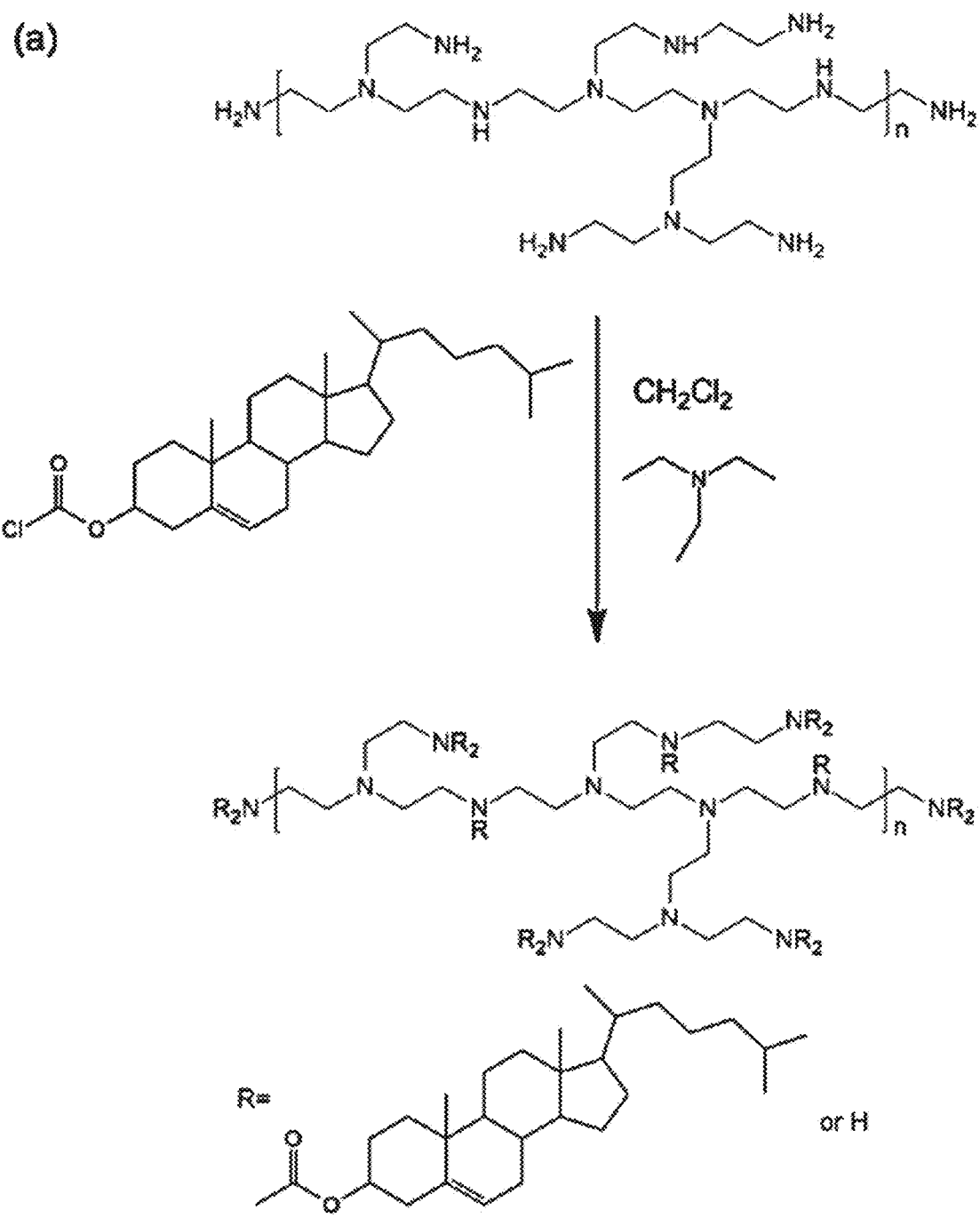
FIGS. 1A-1C.

A novel bio-adhesive suitable for in vivo and/or underwater medical use is disclosed herein. The bio-adhesive exhibits enhanced in vivo and underwater adhesion performance, with good adhesive strength and biocompatibility. The experimental results included below demonstrate the bio-adhesive's ability to close surgical incisions and reduce the formation of seroma. The results also demonstrate that the bio-adhesive can be used in vivo on hard tissue surfaces and in humid environments. The bio-adhesive maintains its adhesive strength when submerged in water, demonstrating its utility for a variety of surgical conditions as an internal use tissue adhesive.

A. Ingredients

The bio-adhesive can in some instances contain a polyanionic polymer and a polycationic polymer functionalized with a hydrophobic moiety. In some aspects, the functionalized polycationic polymer comprises a polycationic polymer having a hydrophobic moiety. In some aspects, the polyanionic polymer is conjugated to a phenolic moiety.

The polycationic polymer may be any polycationic polymer. In some instances, the polycationic polymer is a pharmaceutically acceptable polymer. In some instances, the polycationic polymer is a biodegradable, absorbable, and/or resorbable polycationic polymer. In some instances, the polycationic polymer is a biopolymer and/or a synthetic polymer. In some instances, the polycationic polymer includes one or more polycationic polymer. Non-limiting examples of polycationic polymers include polyethyleneimine, chitosan, diallyl ammonium chloride, polyamidoamine-epichlorohydrin, or any polymer that includes a primary and/or secondary amine and/or tertiary amine moiety.

The polyanionic polymer may be any polyanionic polymer. In some instances, the polyanionic polymer is a pharmaceutically acceptable polymer. In some instances, the polyanionic polymer is a biodegradable, absorbable, and/or resorbable polyanionic polymer. In some instances, the polyanionic polymer is a biopolymer and/or a synthetic polymer. In some instances, the polyanionic polymer includes one or more polyanionic polymer. Non-limiting examples of polyanionic polymers include a negatively-charged polysaccharide. Non-limiting examples of negatively-charged polysaccharides include chondroitin sulfate, glycosaminoglycan, carrageenan, gum Arabic, alginate, xanthan, guar gum, pectin, sodium alginate, hyaluronic acid, gellan gum, heparin, and combinations thereof.

The low wet adhesion strength of many currently available medical grade adhesives is caused by their highly hydrated forms. As such, the inventors incorporated hydrophobic moieties to enhance the bio-adhesive hydrophobicity. Hydrophobic moieties may help impart water-resistance to the bio-adhesive. In some aspects, a hydrophobic moiety is conjugated to the polycationic polymer. In some aspects, the hydrophobic moiety is conjugated to the polyanionic polymer. In some instances, the hydrophobic moiety conjugated polymer is biodegradable, absorbable, and/or resorbable. In some instances, the hydrophobic moiety conjugated polymer is a biopolymer and/or a synthetic polymer. In some instances, the hydrophobic moiety conjugated polymer includes one or more hydrophobic moieties and/or polymers. Non-limiting examples of hydrophobic moieties include stearic acid, oleic acid, lecithins, sulfonate, quaternary ammonium salts, lipids, etc. In some instances, the lipid is cholesterol. Cholesterol is a lipid molecule that is endogenous to the human body, is widely distributed in cell membranes (Farzaneh et al., Gruber et al.) and was employed in the experiments herein for its ability to increase the water-resistance of bio-adhesives. The amount of hydrophobic moieties conjugated to the polymer can be varied to adjust the water-resistance of the bio-adhesive.

Phenolic moieties may help improve adhesion properties. In some instances, a phenolic moiety contains one or more hydroxyl groups. In some aspects, the phenolic moiety is conjugated to the polyanionic polymer. In some aspects, the phenolic moiety is conjugated to the polycationic polymer. In some instances, the phenolic moiety conjugated polymer is biodegradable, absorbable, and/or resorbable. In some instances, the phenolic moiety conjugated polymer is a biopolymer and/or a synthetic polymer. In some instances, the phenolic moiety conjugated polymer includes one or more phenolic moieties and/or polymers. Non-limiting examples of phenolic moieties include catechol groups. Catechol groups may polymerize or oxidize under alkaline environments. Non-limiting examples of phenolic moieties include catechol, catechin, dopamine, levopamine, epicatechin, or any compound that includes an aromatic ring and at least two hydroxyl groups. Catechin is mainly sourced from plants, widely studied as an antioxidant, and furnished with catechol groups (He et al., Pheomphun et al.). The amount of phenolic moieties conjugated to the polymer can be varied to adjust the adhesiveness of the bio-adhesive.

In some aspects, the bio-adhesive comprises from 15 to 60% by weight, based on a total weight of the bio-adhesive, of the polycationic polymer (e.g., polycationic polymer functionalized with a hydrophobic moiety). The bio-adhesive can include an amount of polycationic polymer that is any one of, less than, greater than, or between 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 wt. %, or any range derivable therein.

In some aspects, the bio-adhesive comprises from 40 to 85% by weight, based on a total weight of the bio-adhesive, of the polyanionic polymer (e.g., phenolic moiety conjugated polyanionic polymer). The bio-adhesive can include an amount of polyanionic polymer that is any one of, less than, greater than, or between 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, or 85 wt. %, or any range derivable therein.

In some aspects, the ratio of hydrophobic moieties conjugated to the polymer may be 4 hydrophobic moieties to each subunit of the polymer (4:1) to 1 hydrophobic moiety to 15 subunits of the polymer (1:15). In some instances, the ratio of hydrophobic moieties conjugated to the polymer may be any one of, less than, greater than, or between 4:1, 3:1, 2:1, 3:2, 1:1, 2:3, 1:2, 1:3, 1:4, 1:5, 1:6, 1:7, 1:8, 1:9, 1:10, 1:11, 1:12, 1:13, 1:14, 1:15, or any range derivable therein.

In some aspects, the ratio of phenolic moieties conjugated to the polymer may be 4 phenolic moieties to each subunit of the polymer (4:1) to 1 phenolic moiety to 15 subunits of the polymer (1:15). In some instances, the ratio of phenolic moieties conjugated to the polymer may be any one of, less than, greater than, or between 4:1, 3:1, 2:1, 3:2, 1:1, 2:3, 1:2, 1:3, 1:4, 1:5, 1:6, 1:7, 1:8, 1:9, 1:10, 1:11, 1:12, 1:13, 1:14, 1:15, or any range derivable therein.

The weight average molecular weight (Mw) of the polyanionic polymers employed herein is not particularly limited. Polyanionic polymers molecular weights ranging from 100 to 1,000,000 g/mole or greater can be employed in the bio-adhesives disclosed herein. The Mw of the polyanionic polymers employed herein can include any one of, less than, greater than, or between 100, 200, 300, 400, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 5100, 5200, 5300, 5400, 5500, 5600, 5700, 5800, 5900, 6000, 6100, 6200, 6300, 6400, 6500, 6600, 6700, 6800, 6900, 7000, 7100, 7200, 7300, 7400, 7500, 7600, 7700, 7800, 7900, 8000, 8100, 8200, 8300, 8400, 8500, 8600, 8700, 8800, 8900, 9000, 9100, 9200, 9300, 9400, 9500, 9600, 9700, 9800, 9900, 10000, 11000, 12000, 13000, 14000, 15000, 16000, 17000, 18000, 19000, 20000, 21000, 22000, 23000, 24000, 25000, 26000, 27000, 28000, 29000, 30000, 31000, 32000, 33000, 34000, 35000, 36000, 37000, 38000, 39000, 40000, 41000, 42000, 43000, 44000, 45000, 46000, 47000, 48000, 49000, 50000, 51000, 52000, 53000, 54000, 55000, 56000, 57000, 58000, 59000, 60000, 61000, 62000, 63000, 64000, 65000, 66000, 67000, 68000, 69000, 70000, 71000, 72000, 73000, 74000, 75000, 76000, 77000, 78000, 79000, 80000, 81000, 82000, 83000, 84000, 85000, 86000, 87000, 88000, 89000, 90000, 91000, 92000, 93000, 94000, 95000, 96000, 97000, 98000, 99000, 100000, 110000, 120000, 130000, 140000, 150000, 160000, 170000, 180000, 190000, 200000, 210000, 220000, 230000, 240000, 250000, 260000, 270000, 280000, 290000, 300000, 310000, 320000, 330000, 340000, 350000, 360000, 370000, 380000, 390000, 400000, 410000, 420000, 430000, 440000, 450000, 460000, 470000, 480000, 490000, 500000, 510000, 520000, 530000, 540000, 550000, 560000, 570000, 580000, 590000, 600000, 610000, 620000, 630000, 640000, 650000, 660000, 670000, 680000, 690000, 700000, 710000, 720000, 730000, 740000, 750000, 760000, 770000, 780000, 790000, 800000, 810000, 820000, 830000, 840000, 850000, 860000, 870000, 880000, 890000, 900000, 910000, 920000, 930000, 940000, 950000, 960000, 970000, 980000, 990000, 1000000 g/mole or any Mw therebetween or any range thereof. In some instances, the Mw of the polyanionic polymers employed herein is greater than 15000 daltons (Da), 20000 Da, 25000 Da, 30000 Da, 35000 Da, 40000 Da, 45000 Da, 50000, 55000 Da, or 60000 Da or any number therebetween or range thereof. In some instances, the polyanionic polymer is chondroitin sulfate that has a molecular weight greater than 25000 Da, 30000 Da, 35000 Da, 40000 Da, 45000 Da, 50000, 55000 Da, or 60000 Da or any number therebetween or range thereof.

The weight average molecular weight (Mw) of the polycationic polymers, e.g., polyethyleneimine, employed herein is not particularly limited. Polycationic polymers molecular weights ranging from 100 to 1,000,000 g/mole can be employed in the bio-adhesives disclosed herein. The Mw of the polycationic polymers employed herein can include any one of, less than, greater than, or between 100, 200, 300, 400, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 5100, 5200, 5300, 5400, 5500, 5600, 5700, 5800, 5900, 6000, 6100, 6200, 6300, 6400, 6500, 6600, 6700, 6800, 6900, 7000, 7100, 7200, 7300, 7400, 7500, 7600, 7700, 7800, 7900, 8000, 8100, 8200, 8300, 8400, 8500, 8600, 8700, 8800, 8900, 9000, 9100, 9200, 9300, 9400, 9500, 9600, 9700, 9800, 9900, 10000, 11000, 12000, 13000, 14000, 15000, 16000, 17000, 18000, 19000, 20000, 21000, 22000, 23000, 24000, 25000, 26000, 27000, 28000, 29000, 30000, 31000, 32000, 33000, 34000, 35000, 36000, 37000, 38000, 39000, 40000, 41000, 42000, 43000, 44000, 45000, 46000, 47000, 48000, 49000, 50000, 51000, 52000, 53000, 54000, 55000, 56000, 57000, 58000, 59000, 60000, 61000, 62000, 63000, 64000, 65000, 66000, 67000, 68000, 69000, 70000, 71000, 72000, 73000, 74000, 75000, 76000, 77000, 78000, 79000, 80000, 81000, 82000, 83000, 84000, 85000, 86000, 87000, 88000, 89000, 90000, 91000, 92000, 93000, 94000, 95000, 96000, 97000, 98000, 99000, 100000, 110000, 120000, 130000, 140000, 150000, 160000, 170000, 180000, 190000, 200000, 210000, 220000, 230000, 240000, 250000, 260000, 270000, 280000, 290000, 300000, 310000, 320000, 330000, 340000, 350000, 360000, 370000, 380000, 390000, 400000, 410000, 420000, 430000, 440000, 450000, 460000, 470000, 480000, 490000, 500000, 510000, 520000, 530000, 540000, 550000, 560000, 570000, 580000, 590000, 600000, 610000, 620000, 630000, 640000, 650000, 660000, 670000, 680000, 690000, 700000, 710000, 720000, 730000, 740000, 750000, 760000, 770000, 780000, 790000, 800000, 810000, 820000, 830000, 840000, 850000, 860000, 870000, 880000, 890000, 900000, 910000, 920000, 930000, 940000, 950000, 960000, 970000, 980000, 990000, 1000000 g/mole, or any Mw therebetween or any range thereof. In some instances, the Mw of the polycationic polymers employed herein is greater than 15000 daltons (Da), 20000 Da, 25000 Da, 30000 Da, 35000 Da, 40000 Da, 45000 Da, 50000, 55000 Da, or 60000 Da or any number therebetween or range thereof. In some instances, the polycationic polymer is polyethyleneimine that has a molecular weight greater than 25000 Da, 30000 Da, 35000 Da, 40000 Da, 45000 Da, 50000, 55000 Da, or 60000 Da or any number therebetween or range thereof.

Chondroitin sulfate (CS) and glycosaminoglycan (GAG) are derived from cartilage, and have been employed in the experiments herein as a non-limiting example of biocompatible, polyanionic base materials (Zhu et al. 2019, Tao et al.). CS is a negatively charged polysaccharide and can integrate with positively charged materials through electrostatic interactions (Jin et al.). As a non-limiting example of phenolic moieties, phenolic catechols, which can polymerize or oxidize under alkaline environments, were conjugated to the polyanionic components in the experiments herein for their effect on adhesiveness. Branched polyethylenimine (PEI), a non-limiting example of a positively charged polymer, has been widely investigated in gene therapy, antimicrobial, and bio-adhesive applications (Wang et al., Ren et al., Cui et al.). PEI has been employed in the experiments herein. A novel bio-adhesive, referred to herein as PcC, suitable for, but not limited to, underwater and medical use is disclosed herein.

B. Structure

The compositions of the present invention can be structured or formulated into a variety of different forms. Non-limiting examples include powders, solutions (e.g., aqueous, hydro-alcoholic), emulsions (e.g., water-in-oil, water-in-oil-in-water, oil-in-water, silicone-in-water, water-in-silicone, oil-in-water-in-oil, oil-in-water-in-silicone emulsions), creams, anhydrous bases, gels (e.g., hydrogel), etc. Variations and other structures will be apparent to the skilled artisan and are appropriate for use in the present invention. In some instances, the ingredients for making the bio-adhesive are stored separated or at least partially separated and combined right before, or during application to the object to be adhered. In some instances, the ingredients are stored at least partially separated until 10, 9, 8, 7, 6, 5, 4, 3, 2, or 1 minute or 55, 50, 45, 40, 35, 30, 25, 20, 15, 10, 5, 4, 3, 2, or 1 second, or any time therebetween or range thereof before application to the object to be adhered. In some instances, the ingredients are at least partially separated and at least one of the ingredients are stored in solution or as a dry ingredient before being combined with the other ingredients or applied to the object to be adhered. In some instances, the ingredients are hydrated with water to form the bio-adhesive right before, or during application to the object to be adhered. In some instances, the ingredients are hydrated 10, 9, 8, 7, 6, 5, 4, 3, 2, or 1 minute or 55, 50, 45, 40, 35, 30, 25, 20, 15, 10, 5, 4, 3, 2, or 1 second, or any time therebetween or range thereof before application to the object to be adhered.

The compositions of the present invention can include or be incorporated into all types of vehicles and carriers, or may not include a vehicle or carrier. The vehicle or carrier can be a pharmaceutically acceptable vehicle or carrier. Non-limiting examples of vehicles or carriers include water, glycerin, alcohol, oil, a silicon containing compound, a silicone compound, etc. Variations and other appropriate vehicles will be apparent to the skilled artisan and are appropriate for use in the present invention. In certain aspects, the concentrations and combinations of the compounds, ingredients, and agents can be selected in such a way that the combinations are chemically compatible and do not form complexes which precipitate from the finished product.

C. Additional Ingredients

In addition to the combination of ingredients disclosed by the inventors, the compositions can also include additional ingredients. Non-limiting examples of these additional ingredients may include, but are not limited to pharmaceutical active ingredients, thickening agents, preservatives, vehicles, carriers, dyes and color ingredients, etc.

The compositions can also include any number of combinations of additional ingredients described throughout this specification (e.g., color ingredients, preservative, or additional pharmaceutical ingredients). The concentrations of any ingredient within the compositions can vary. In non-limiting embodiments, for example, the compositions can comprise, consist essentially of, or consist of, in their final form, for example, at least about 0.0001%, 0.0002%, 0.0003%, 0.0004%, 0.0005%, 0.0006%, 0.0007%, 0.0008%, 0.0009%, 0.0010%, 0.0011%, 0.0012%, 0.0013%, 0.0014%, 0.0015%, 0.0016%, 0.0017%, 0.0018%, 0.0019%, 0.0020%, 0.0021%, 0.0022%, 0.0023%, 0.0024%, 0.0025%, 0.0026%, 0.0027%, 0.0028%, 0.0029%, 0.0030%, 0.0031%, 0.0032%, 0.0033%, 0.0034%, 0.0035%, 0.0036%, 0.0037%, 0.0038%, 0.0039%, 0.0040%, 0.0041%, 0.0042%, 0.0043%, 0.0044%, 0.0045%, 0.0046%, 0.0047%, 0.0048%, 0.0049%, 0.0050%, 0.0051%, 0.0052%, 0.0053%, 0.0054%, 0.0055%, 0.0056%, 0.0057%, 0.0058%, 0.0059%, 0.0060%, 0.0061%, 0.0062%, 0.0063%, 0.0064%, 0.0065%, 0.0066%, 0.0067%, 0.0068%, 0.0069%, 0.0070%, 0.0071%, 0.0072%, 0.0073%, 0.0074%, 0.0075%, 0.0076%, 0.0077%, 0.0078%, 0.0079%, 0.0080%, 0.0081%, 0.0082%, 0.0083%, 0.0084%, 0.0085%, 0.0086%, 0.0087%, 0.0088%, 0.0089%, 0.0090%, 0.0091%, 0.0092%, 0.0093%, 0.0094%, 0.0095%, 0.0096%, 0.0097%, 0.0098%, 0.0099%, 0.0100%, 0.0200%, 0.0250%, 0.0275%, 0.0300%, 0.0325%, 0.0350%, 0.0375%, 0.0400%, 0.0425%, 0.0450%, 0.0475%, 0.0500%, 0.0525%, 0.0550%, 0.0575%, 0.0600%, 0.0625%, 0.0650%, 0.0675%, 0.0700%, 0.0725%, 0.0750%, 0.0775%, 0.0800%, 0.0825%, 0.0850%, 0.0875%, 0.0900%, 0.0925%, 0.0950%, 0.0975%, 0.1000%, 0.1250%, 0.1500%, 0.1750%, 0.2000%, 0.2250%, 0.2500%, 0.2750%, 0.3000%, 0.3250%, 0.3500%, 0.3750%, 0.4000%, 0.4250%, 0.4500%, 0.4750%, 0.5000%, 0.5250%, 0.5550%, 0.5750%, 0.6000%, 0.6250%, 0.6500%, 0.6750%, 0.7000%, 0.7250%, 0.7500%, 0.7750%, 0.8000%, 0.8250%, 0.8500%, 0.8750%, 0.9000%, 0.9250%, 0.9500%, 0.9750%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3% 5.4% 5.5%, 5.6%, 5.7% 5.8%, 5.9% 6.0%, 6.1%, 6.2%, 6.3%, 6.4%, 6.5%, 6.6%, 6.7%, 6.8%, 6.9%, 7.0%, 7.1%, 7.2%, 7.3% 7.4% 7.5%, 7.6%, 7.7% 7.8%, 7.9%, 8.0%, 8.1%, 8.2%, 8.3%, 8.4%, 8.5%, 8.6%, 8.7%, 8.8%, 8.9%, 9.0%, 9.1%, 9.2%, 9.3%, 9.4%, 9.5%, 9.6%, 9.7%, 9.8%, 9.9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 60%, 65%, 70%, 75%, 80%, 85%, 90%, 95%, or 99% or any range derivable therein, of at least one of the ingredients that are mentioned throughout the specification and claims. In non-limiting aspects, the percentage can be calculated by weight or volume of the total composition. A person of ordinary skill in the art would understand that the concentrations can vary depending on the addition, substitution, and/or subtraction of ingredients in a given composition.

Non-limiting examples of pharmaceutical active ingredients can include, but are not limited to analgesics, anesthetics, antihistamines, alpha-adrenergic receptor agonists, anti-inflammatory agents including non-steroidal anti-inflammatory drugs, antibiotics, antifungals, antivirals, antimicrobials, anti-cancer actives, antineoplastics, antipruritics, antiseborrheic agents, biologically active proteins and peptides, burn treatment agents, cauterizing agents, enzymes, hemostatics, steroids including hormones and corticosteroids, vasoconstrictors, wound treatment agents, wound healing agents, etc.

Non-limiting examples of thickening agents can include, but are not limited to thickener or gelling agents, including substances which can increase the viscosity of a composition. Thickeners include those that can increase the viscosity of a composition without substantially modifying the efficacy of the active ingredient within the composition. Thickeners can also increase the stability of compositions. In certain aspects of the present invention, thickeners include hydrogenated polyisobutene, trihydroxystearin, ammonium acryloyldimethyltaurate/vp copolymer, or a mixture of them.

Non-limiting examples of additional thickening agents include carboxylic acid polymers, crosslinked polyacrylate polymers, polyacrylamide polymers, polysaccharides, and gums. Examples of carboxylic acid polymers include crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol. Examples of commercially available carboxylic acid polymers include carbomers, which are homopolymers of acrylic acid crosslinked with allyl ethers of sucrose or pentaerytritol. Non-limiting examples of crosslinked polyacrylate polymers include cationic and nonionic polymers. Non-limiting examples of polyacrylamide polymers (including nonionic polyacrylamide polymers including substituted branched or unbranched polymers) include polyacrylamide, isoparaffin and laureth-7, multi-block copolymers of acrylamides and substituted acrylamides with acrylic acids and substituted acrylic acids. Non-limiting examples of polysaccharides include cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Another example is an alkyl substituted cellulose where the hydroxy groups of the cellulose polymer is hydroxyalkylated (preferably hydroxy ethylated or hydroxypropylated) to form a hydroxyalkylated cellulose which is then further modified with a C10-C30 straight chain or branched chain alkyl group through an ether linkage. Typically these polymers are ethers of C10-C30 straight or branched chain alcohols with hydroxyalkylcelluloses. Other useful polysaccharides include scleroglucans comprising a linear chain of (1-3) linked glucose units with a (1-6) linked glucose every three units. Non-limiting examples of gums include acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluronic acid, hydrated silica, hydroxypropyl chitosan, hydroxypropyl guar, karaya gum, kelp, locust bean gum, natto gum, potassium alginate, potassium carrageenan, propylene glycol alginate, sclerotium gum, sodium carboxymethyl dextran, sodium carrageenan, tragacanth gum, xanthan gum, and mixtures thereof.

Non-limiting examples of analgesics include substances able to reduce pain. Analgesics can include, but are not limited to lidocaine, wintergreen oil, terpenes such as guaiacol, diclofenac, ketoprofen, capsaicin, rubefacients, nonsteroidal anti-inflammatory drugs, morphine, hydromorphone, other opioids such as tramadol, pethidine, codeine, piritramide, levomethadone, fentanyl, alfentanil, remifentanil and sufentanil.

Non-limiting examples of preservatives include antimicrobial agents, antifungal agents, antivirals, antimicrobials, anti-oxidants, chelating agents, parabens, phenols, acids, and alcohols.

Non-limiting examples of dyes and color ingredients include Blue 1, Blue 1 Lake, Red 40, titanium dioxide, D&C blue no. 4, D&C green no. 5, D&C orange no. 4, D&C red no. 17, D&C red no. 33, D&C violet no. 2, D&C yellow no. 10, D&C yellow no. 11, etc.

D. Making

The bio-adhesives disclosed herein can be prepared relatively rapidly, e.g., in a few seconds, thereby making the bio-adhesives expedient for medical applications. In some instances, the ingredients for making the bio-adhesive are stored separated or at least partially separated from each other and combined right before, or during application to the object to be adhered. In some instances, the ingredients are stored at least partially separated until 10, 9, 8, 7, 6, 5, 4, 3, 2, or 1 minute or 55, 50, 45, 40, 35, 30, 25, 20, 15, 10, 5, 4, 3, 2, or 1 second, or any time therebetween or range thereof before application to the object to be adhered. In some instances, the ingredients are at least partially separated and at least one of the ingredients are stored in solution or as a dry ingredient before being combined with the other ingredients or applied to the object to be adhered. In some instances, the ingredients are hydrated with water to form the bio-adhesive right before, or during application to the object to be adhered. In some instances, the ingredients are hydrated 10, 9, 8, 7, 6, 5, 4, 3, 2, or 1 minute or 55, 50, 45, 40, 35, 30, 25, 20, 15, 10, 5, 4, 3, 2, or 1 second, or any time therebetween or range thereof before application to the object to be adhered.

In some instances, the bio-adhesive can be formed by mixing the polyanionic polymer(s) (e.g., phenolic moiety conjugated polyanionic polymer) and the polycationic polymer(s) (e.g., polycationic polymer functionalized with a hydrophobic moiety). The bio-adhesive can be fabricated based on both electrostatic interactions, such as via electrostatic interaction crosslinking, and exposure of one or more hydrophobic moiety on the surface of the polymer(s). However, the mixtures of the polyanionic polymer(s) (e.g., phenolic moiety conjugated polyanionic polymer) and the polycationic polymer(s) (e.g., polycationic polymer functionalized with a hydrophobic moiety) may remain soluble in water, indicating the hydrophobic moiety may be exposed after crosslinking and contribute to the bio-adhesive formation. In some instances, the bio-adhesive forms as a gel. In addition, the phenolic moiety (e.g., hydroxyl groups on the phenolic moiety) in some instances may be oxidized or polymerized under an environment introduced by the polycationic polymer(s). The oxidation or polymerization may contribute to the adhesive properties of the bio-adhesive.

The polyanionic polymer(s) (e.g., phenolic moiety conjugated polyanionic polymer) and the polycationic polymer(s) (e.g., polycationic polymer functionalized with a hydrophobic moiety) can be mixed at a weight ratio of 5:1, 4:1, 3:1, 2:1, 3:2, 1:1, 2:3, 1:2, 1:3, 1:4, 1:5, or any ratio therebetween or range thereof.

The bio-adhesive can be easy to prepare, with a crosslinking reaction forming the bio-adhesive that can be finished within 1 minute or 55, 50, 45, 40, 35, 30, 25, 20, 15, 10, 5, 4, 3, 2, or 1 second, or any time therebetween or range thereof, such as 5 seconds facilitated by agitation.

In some instances, the functionalized polycationic polymer can be formed by a reaction between primary or secondary or tertiary amine and acyl chloride groups. In a non-limiting example, a chlorinated hydrophobic moiety, such as cholesterol chloroformate can be reacted with an amine containing polycationic polymer, such as polyethyleneimine. In some instances, the reaction can be in the presence of triethylamine (TEA). In some instances, the polycationic polymer and or hydrophobic moiety can be dissolved in dichloromethane (DCM). In some instances, the reaction can occur for 1, 2, 3, 4, 5, 6, 7, 8, 9, 10, 11, 12, 13, 14, 15, 16, 17, 18, 19, 20, 21, 22, or hours, or 1, 2, 3, or 4 days, or any time therebetween or range thereof, and at a temperature of −20, −15, −10, −5, 0, 5, 10, 15, 20, 25, 30, 35, 40, 45, or 50° C., or any temperature therebetween or range thereof. The products can be purified, such as by distillation, dialysis, and/or washes. In some instances, the products can be dried.

In some instances, the phenolic moiety conjugated polyanionic polymer can be formed by a reaction between free radicals induced on the polyanionic polymer that react with the phenolic moiety, such as a phenolic moiety containing two or more hydroxyl group. In a non-limiting example, free radicals can be formed on a polyanionic polymer by induction by a redox pair, such as hydrogen peroxide and ascorbic acid. The phenolic moiety, such as catechin, can be reacted with the induced free radical on the polyanionic polymer. In some instances, the reaction can be in the presence of a solvent such as water, or hot water. In some instances, the free radical induction can occur for 30, 40, 50, 60, 70, 80, 90, 100, 110, 120, 130, 140, 150, 160, 170 minutes or 3, 3.5, 4, 4.5, 5, 5.5, 6, 6.5, or more hours, or time therebetween or range thereof. In some instances, the free radical induction can occur at 5, 10, 15, 20, 25, 30, 35, 40, 45, 50, 55, 60, 65° C. or temperature therebetween or range thereof. In some instances, the reaction can occur for 5, 6, 7, 8, 9, 10, 11, 12, 13, 14, 15, 16, 17, 18, 19, 20, 21, 22, or hours, or 1, 2, 3, or 4 days, or any time therebetween or range thereof, and at a temperature of −20, −15, −10, −5, 0, 5, 10, 15, 20, 25, 30, 35, 40, 45, or 50° C., or any temperature therebetween or range thereof. The products can be purified, such as by distillation, dialysis, and/or washes. In some instances, the products can be dried.

E. Uses

The bio-adhesive disclosed herein can be used to adhere to two or more surfaces. The surfaces can be from the same object or different objects, such as a biological surface. In some instances, the two surfaces are two surfaces of the same wound, two surfaces of the same skin, two surfaces of the same organ, or two surfaces of the same organism. In some instances one or both of the surfaces are a hard tissue, such as cartilage, bone, shell, claw, tooth, and/or nail. In some instances one or both of the surfaces are wet or underwater when the surface is contacted with the bio-adhesive. In some instances, one or both of the surfaces are hard tissue and wet or underwater when the surface is contacted with the bio-adhesive. One or both of the surfaces may be a surface of a non-biological material. In some instances, one or both of the surfaces are of a medical device. In some instances, one of the surfaces is a surface of a biological material and one of the surfaces is a surface of a non-biological material, such as a medical device. In some instances, the two surfaces are from two different objects. In some instances, the bio-adhesive used in the method is any one of the bio-adhesives disclosed herein.

In some aspects, the bio-adhesive can be prepared within 10, 9, 8, 7, 6, 5, 4, 3, 2, or 1 minute or 55, 50, 45, 40, 35, 30, 25, 20, 15, 10, 5, 4, 3, 2, or 1 second, or any time therebetween or range thereof, before application to the surface. In some aspects, the bio-adhesive is prepared hours, days, months, or years before application to the surface, such as a dry bio-adhesive.

In some aspects, the bio-adhesive can rapidly cure or set. In some instances, the bio-adhesive can cure and/or set within 10, 9, 8, 7, 6, 5, 4, 3, 2, or 1 minute or 55, 50, 45, 40, 35, 30, 25, 20, 15, 10, 5, 4, 3, 2, or 1 second, or any time therebetween or range thereof, after application to the surface.

In some aspects, the bio-adhesive can be used in or on a human, another mammal, another animal, or a plant. In some aspects, the bio-adhesive is used during surgery and/or after surgery to repair the surgical sight.

F. Kits

The bio-adhesive disclosed herein can be comprised in an adhesive kit. The ingredients to prepare the bio-adhesive disclosed herein can be comprised in an adhesive kit. The adhesive kit can be used to perform any of the methods or procedures disclosed herein. The ingredients and/or the bio-adhesive of the kit can be any of the ingredients and/or bio-adhesive disclosed herein. In some instances, the adhesive kit is a medical adhesive kit. The medical adhesive kit can be used in some instances for adhering biological materials together and/or a biological material to a non-biological material together. The medical adhesive kit can be used in some instances in surgery or as part of a medical emergency kit. The adhesive kit can in some instances, be used to prepare the bio-adhesive disclosed herein.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Negatively-charged catechin modified CS (CSCC) was prepared by employing a free radical-induced mechanism. Positively-charged cholesterol chloroformate-modified branched PEI (PEI-Chol) was prepared through the reaction between primary, secondary, and/or tertiary PEI amines and cholesterol acyl chlorides. The chemical structures and cytotoxicity were characterized.

Figure 2A:
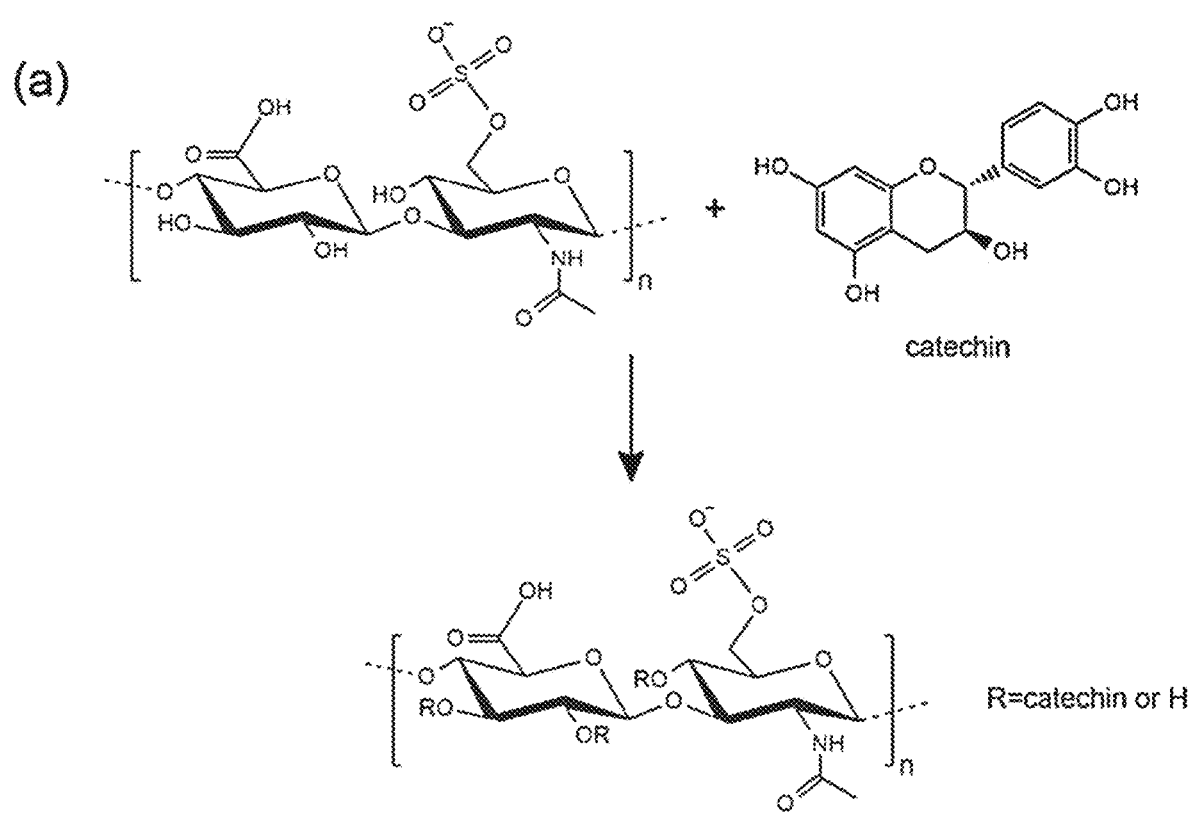
FIGS. 2A-2C.

Preparation of CSCC—CSCC was prepared by employing a free radical-induced mechanism (FIG. 2A) (Spizzirri et al.). 0.5 g of CS was dissolved in 10 mL deionized (DI) water (5 wt %) in a round-bottom flask. A redox pair of $H_2O_2$ (4 mL) and ascorbic acid (0.19 g) was added, after which the mixture was stirred at room temperature (RT) for 2 h to generate free radicals. 0.4 g of catechin (CC) was dissolved in 25 mL hot DI water (60° C.) and added to the reaction mixture. The reaction mixture was then cooled to RT and maintained under RT for 48 hours. The product was collected, dialyzed against DI water for 2 days in a dialysis bag (MWCO: 2000 Da), lyophilized (FreezeZone, Labconco) and kept at 4° C. for further use.

Preparation of PEI-Chol—PEI-Chol was prepared through the reaction between primary, secondary, or tertiary PEI amine and cholesterol in acyl chloride form (FIG. 1A). First, 1.85 g of branched PEI (Mw=25000 Da) was dissolved in 20 mL dichloromethane (DCM) and added together with 186 µL triethylamine (TEA) into a two-neck flask in an ice bath. 0.2 g of cholesterol chloroformate (Chol) was then dissolved in 5 mL DCM and added to the mixture dropwise via a dropping funnel. The mixture was stirred overnight at 0° C., after which the DCM was removed by reduced pressure distillation. The product was washed with diethyl ether to remove unreacted Chol and TEA and purified in vacuo at ambient temperature.

Figure 1B:
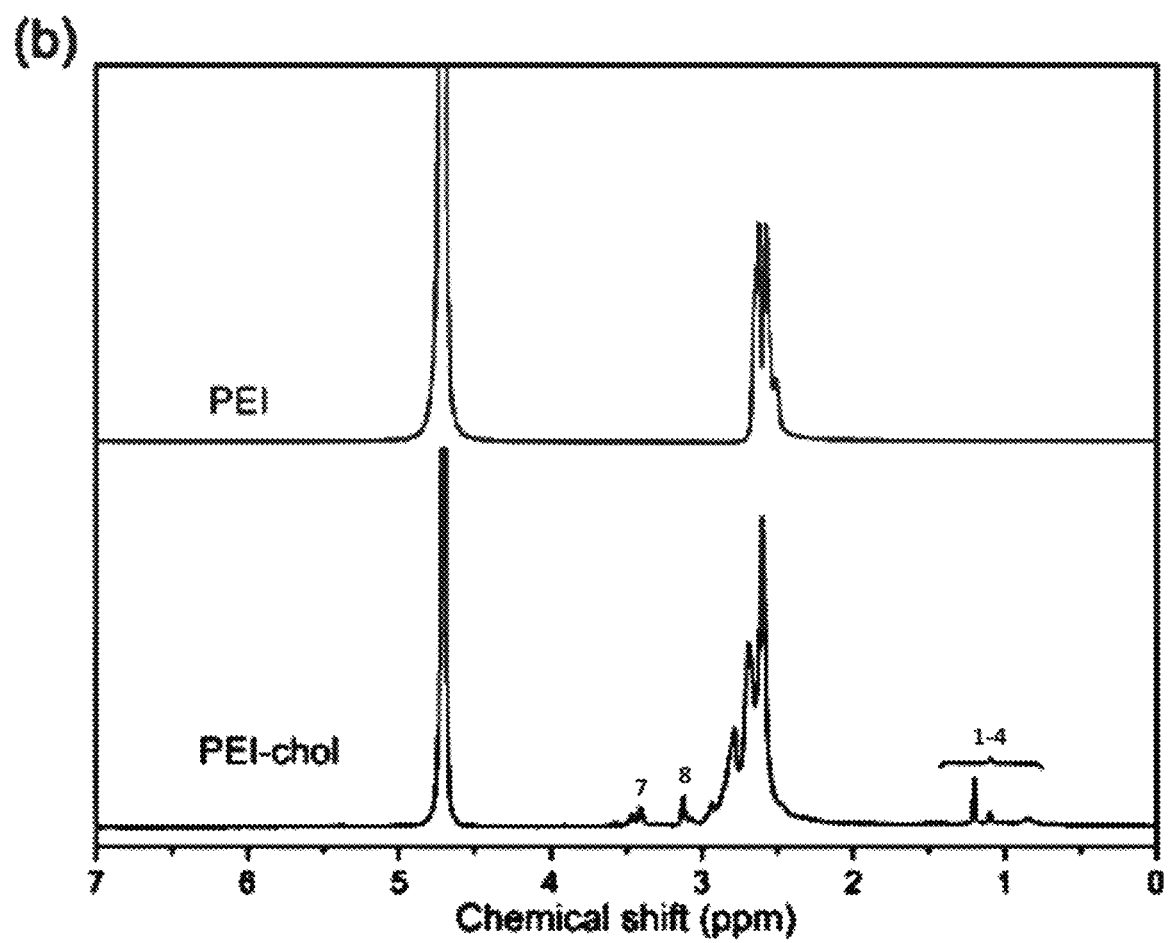
Figure 1C:
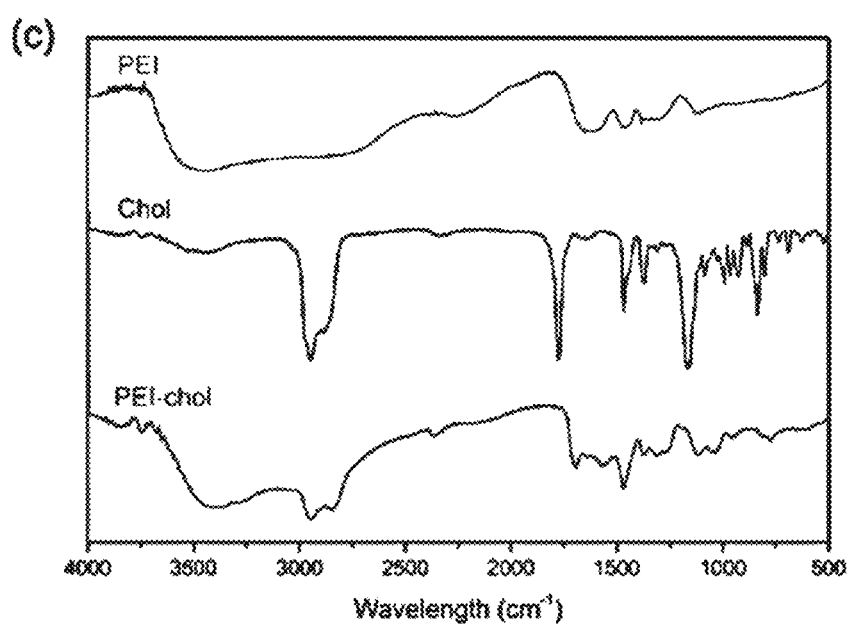

Characterization of chemical structure of CSCC and PEI-Chol—Chemical structures of CSCC and PEI-Chol were characterized by proton nuclear magnetic resonance ($^1$H NMR) spectroscopy (Bruker 600 MHz "ASCEND AVANCE III HD" Nuclear Magnetic Resonance System) with deuterium oxide ($D_2O$) as the solvent, and fourier transform infrared (FTIR) spectroscopy (Perkin Elmer Spectrum 100). As shown in the $^1$H NMR spectrum of PEI-Chol (FIG. 1$i$), peaks at around 3.5 ppm, 3.1 ppm, and from 0.5 to 1.5 ppm belong to cholesterol, confirming the successful conjugation of PEI with cholesterol. The more apparent C—H stretching vibration at around 2900 cm$^{-1}$ on the FTIR spectrum of PEI-Chol compared to that of PEI further confirmed that cholesterol was successfully grafted onto PEI (FIG. 1C).

Figure 2B:
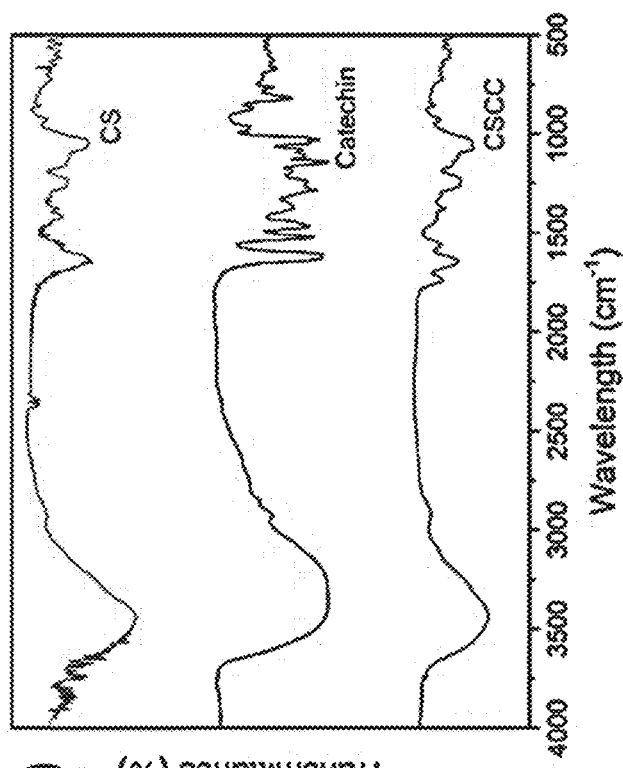
Figure 2C:
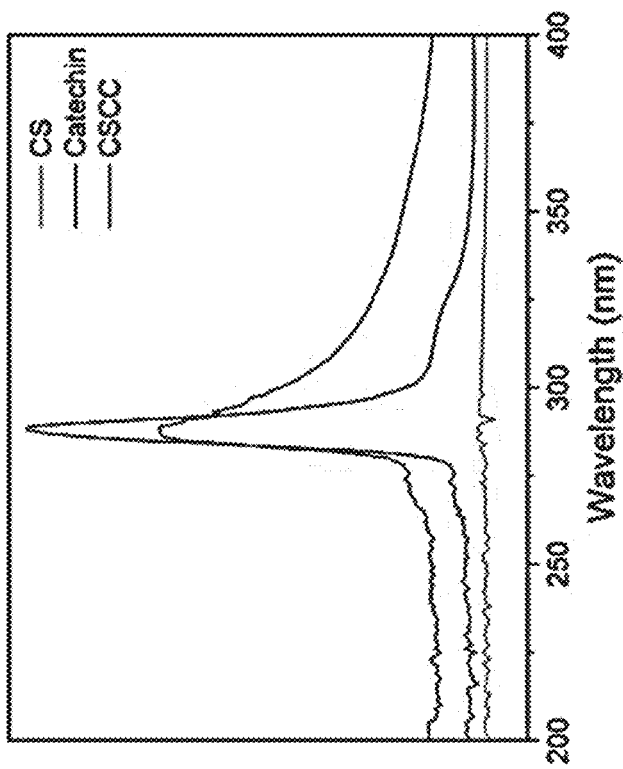

As shown in the UV-vis spectra for CSCC (FIG. 2B), a prominent peak around 290 nm was observed. This peak corresponds to the benzene ring of catechin, and confirmed the successful grafting of catechins. The peak at around 1736 cm$^{-1}$ on the FTIR spectrum of CSCC represents C=C stretching vibration, also confirming the successful synthesis of CSCC (FIG. 2C).

In vitro cytotoxicity—CSCC or PEI-Chol can possibly be released from PcC bio-adhesive during in vivo application. Therefore, an in vitro cytotoxicity test was carried out using the CCK-8 reagent to detect the PEI-Chol or CSCC safe-use concentration limit for the adhesive's potential medical use (FIG. 6A through FIG. 6F). In vitro cytotoxicity of CSCC and PEI-Chol on cells was evaluated using a cell proliferation reagent CCK-8 assay kit (Cell Counting Kit-8, Beyotime). First, L929 cells (ATCC) were cultured in 96 well plates (2500 cells/well) with DMEM culture medium with and without CSCC or PEI-Chol. CSCC of different concentrations (4 mg/mL, 2 mg/mL, 1 mg/mL, 0.5 mg/mL, 0.25 mg/mL, 0.125 mg/mL) and PEI-Chol of different concentrations (1.5625 µg/mL, 3.125 µg/mL, 6.25 µg/mL, 12.5 µg/mL, 25 µg/mL, 50 µg/mL) were employed. The mixtures were incubated at 37° C. in a $CO_2$ incubator. CCK-8 reagent was added to each well on days 1, 4 and 7 at a volume ratio of 1:10. The mixtures were then incubated together with cells for 4 h at 37° C. in a $CO_2$ incubator. The absorbance of the incubated mixture was measured and calculated on a microplate reader based on the manufacturer's protocol.

According to the results (see FIG. 6A through FIG. 6F), PEI-Chol aqueous solutions with concentrations greater than 25 µg/mL showed significant cytotoxicity on L929. After the concentration decreased to 12.5 µg/mL, the cytotoxicity of PEI-Chol was highly alleviated. However, a decrease in the cell viability was observed from 81.5±10.0% to 61.6±16.6% from day 1 to day 7. For PEI-Chol aqueous solutions having a concentration less than 6.25 g/mL, no cytotoxicity was detected. Furthermore, the cell proliferation or metabolism cultures with 6.25 µg/mL, 3.125 µg/mL and 1.5625 µg/mL PEI-Chol as additives were facilitated on day 4 (218.8±21.6%, 250.3±3 7.0%, and 185.0±32.9% for 6.25 µg/mL, 3.125 µg/mL and 1.5625 µg/mL groups, respectively) but back to around 110% on day 7. Therefore, PEI-Chol aqueous solutions having a concentration of less than 6.25 µg/mL are safe for cells. For CSCC, 4 mg/mL CSCC aqueous solutions showed cytotoxicity on L929, whereas CSCC aqueous solutions having concentrations less than 2 mg/mL were determined to be safe for cells. Moreover, CSCC concentrations of 2 mg/mL and 1 mg/mL were determined to facilitate cell proliferation or metabolism.

Example 2

PcC bio-adhesive was prepared and characterized.

Fabrication of PcC bio-adhesive—An aqueous solution of CSCC (100 mg/mL) was mixed with an aqueous solution of PEI-Chol (100 mg/mL) at a volume ratio of 1:1 to obtain the bio-adhesive (PcC). The PcC was orange in color. The adhesive hydrogel was easy to prepare with crosslinking reactions finished within 5 seconds facilitated by agitation.

Example 3

Bio-adhesive adherence properties and mechanism of action were characterized.

Figure 7A:
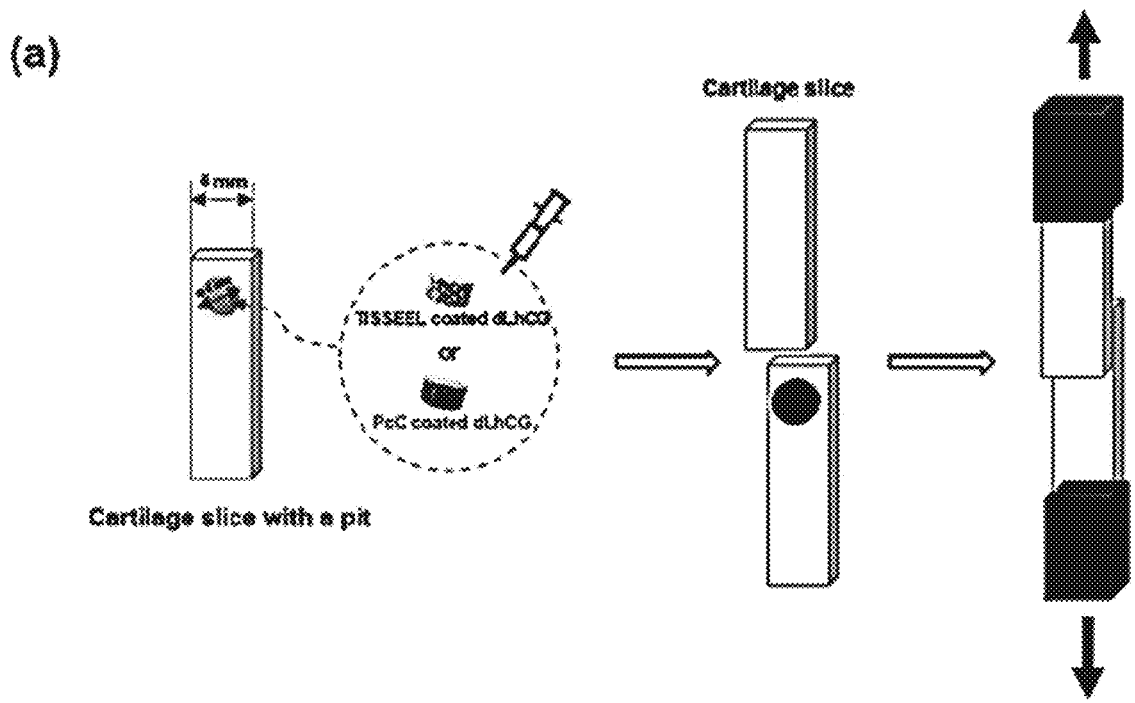
FIGS. 7A-7B.

Lap shear strength test—A lap shear strength test was carried out to measure the adhesion strength of PcC bio-adhesive on cartilage (FIG. 7A). Briefly, cartilage slices were collected from commercially-available porcine bones and cut to approximately µ2×5×30 (mm) each. 40 µL CSCC (100 mg/mL) was mixed with 40 µL PEI-Chol (100 mg/mL) to prepare the bio-adhesive PcC, after which two slices of cartilage were glued together by the PcC bio-adhesive with a lap area of 5 mm×5 mm. The bio-adhesive was dried using a hair dryer for 5 min and subsequently incubated in a 37° C. water bath for 1 h (PcC-W), immersed in water at 37° C. for 1 h (PcC-I) and incubated at ambient environment for 1 h (PcC-A). Decellularized living hyaline cartilage graft (dLhCG) was prepared. Porcine chondrocytes were collected from fresh porcine cartilage, and encapsulated in alginate hydrogel with gelatin microspheres. Extracellular matrix (ECM) was secreted during the growth and proliferation of chondrocytes cultured in the three-dimensional hydrogels. The alginate hydrogels were removed using sodium citrate solution to collect LhCG. Afterwards, decellularization was performed by physical, chemical and enzymatic methods to create dLhCG. Pits were dug into thicker cartilage from the commercially-available porcine bones using a biopunch (φ 4 mm), after which the PcC bio-adhesive-coated dLhCG was placed into the pits. The cartilage was glued to the other piece of cartilage slice, then incubated at 37° C. for 1 h (PcC/dLhCG-W). The samples were fixed using a Tensile Tester (Instron 5942) and pulled at a rate of 2 mm/min. The adhesion strength of TISSEEL® (a commercially-available, fibrin-based bio-adhesive, Shanghai RAAS blood products Co., Ltd) was employed as a control.

Figure 7B:
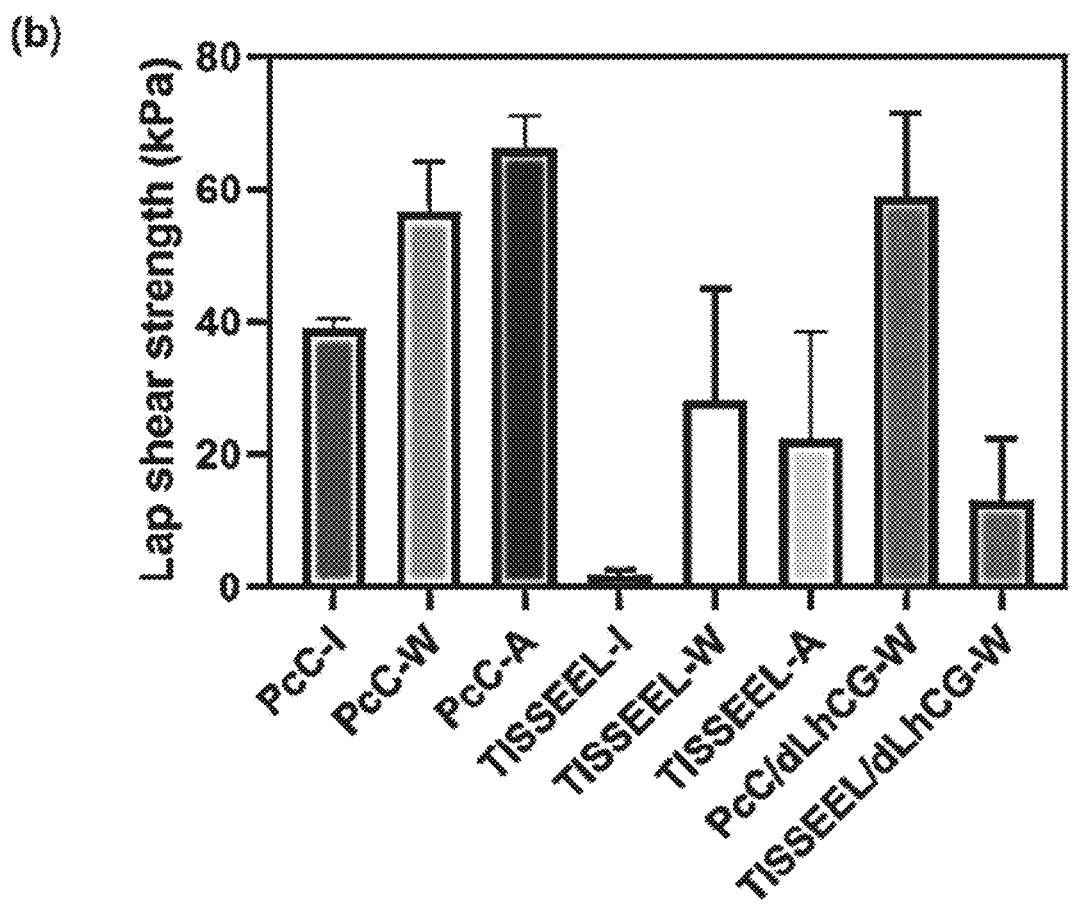

As shown in FIG. 7B, PcC incubated in ambient environment (PcC-A) showed an adhesion strength of 66.3±4.6 kPa. For PcC incubated in a 37° C. water bath (PcC-W), an adhesion strength of 56.7±7.4 kPa was detected. After immersion in a 37° C. water bath (PcC-I), PcC adhesion strength remained at 38.9±1.6 kPa. TISSEEL® incubated in ambient environment (TISSEEL®-A) showed an adhesion strength of 22.3±16.0 kPa. For TISSEEL® incubated in a 37° C. water bath (TISSEEL®-W), the average adhesion strength was 28.1±16.8 kPa. After immersion in a 37° C. water bath (TISSEEL®-I), the adhesive strength declined to 1.9±0.8 kPa, indicating that the bonding properties of TISSEEL® are poor in an aqueous environment.

An in vitro cartilage slices mechanical model was employed (FIG. 7A) to test the mechanical properties of bio-adhesive coated decellularized living hyaline cartilage graft (dLhCG). As shown in FIG. 7B, after incubation in a 37° C. water bath, PcC-coated dLhCG (PcC/dLhCG-W) was 58.6±12.5 kPa, while TISSEEL® coated dLhCG (TISSEEL®/dLhCG-W) showed less strength with 12.9±9.4 kPa.

The lap shear strength analyses demonstrated that the PcC bio-adhesive possesses better adhesive strength than commercially-available fibrin glue TISSEEL®. The PcC bio-adhesive maintains its adhesiveness on wet tissue surfaces or water-submerged environments.

Mechanism of action of PcC bio-adhesive—In order to investigate the mechanism of action of the PcC bio-adhesive, 100 mg/mL aqueous solution of PEI, PEI-Chol and 100 mg/mL aqueous solution of CS, CC, and CSCC were prepared, and different combinations of mixtures were prepared. As is shown in FIG. 3A and FIG. 3B, hydrogels were generated when PEI-Chol was mixed with CSCC or CS, whereas no hydrogel formed when PEI-Chol was mixed with CC. Not to be bound by theory, it is believed that the PcC was formed due to electrostatic interactions between PEI-Chol (positively-charged) and CSCC (negatively-charged). The zeta potential measurement (FIG. 4D) indicates that the yellow CSCC, with a zeta potential of −50.4 mV, interacts with the white PEI-Chol, with a zeta potential of 63.2 mV, to generate the PcC bio-adhesive of orange red color via electrostatic interaction crosslinking. However, the mixtures of PEI with CSCC or CS remained soluble in water, indicating the hydrophobic Chol component was exposed after crosslinking and contributed to the hydrogel formation. The orange red or brick red colors were derived from CC which oxidized or polymerized under the alkaline environment introduced by PEI or PEI-Chol.

Contact angle measurement—The contact angles of water and diiodo-methane on CSCC, PEI-Chol and PcC were measured on a Contact Angle Analyzer (Kruss DSA25) with a water or diiodo-methane drop of 5 L. CSCC, PEI-Chol and PcC were coated on mica and dried at 60° C. in an oven before measurement. The contact angles of water and diiodo-methane on mica were also tested as controls. Contact angle measurement can be used as an indicator of the surface free energy. According to the water contact angle results (FIG. 3C), PcC showed a more hydrophobic surface with a water contact angle of $50.280 \pm 6.720$ compared to that of CSCC ($15.77° + 5.67°$) and PEI-Chol ($26.08° + 5.98°$), further confirming the hydrophobic Chol component was exposed after crosslinking of CSCC and PEI-Chol by electrostatic interactions and contributed to the formation of PcC bio-adhesive.

Figure 4A:
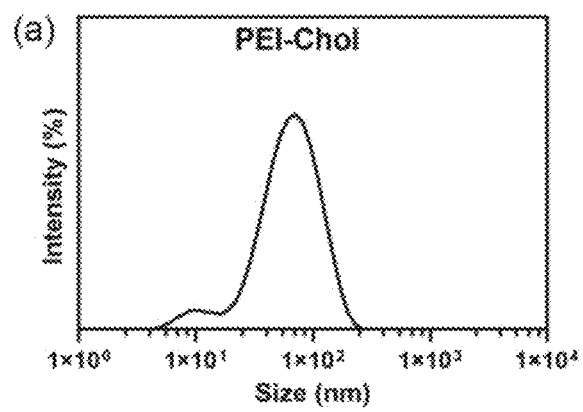
FIGS. 4A-4D.
Figure 4B:
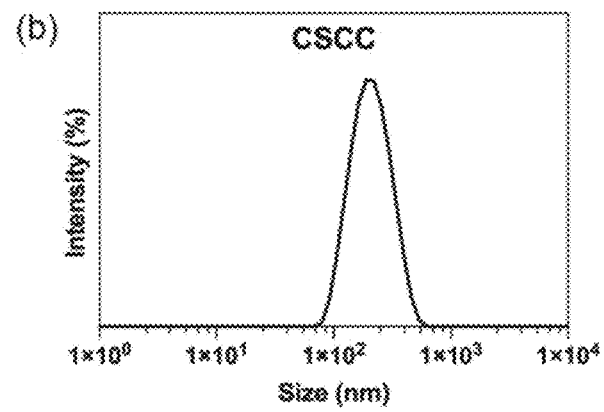
Figure 4C:
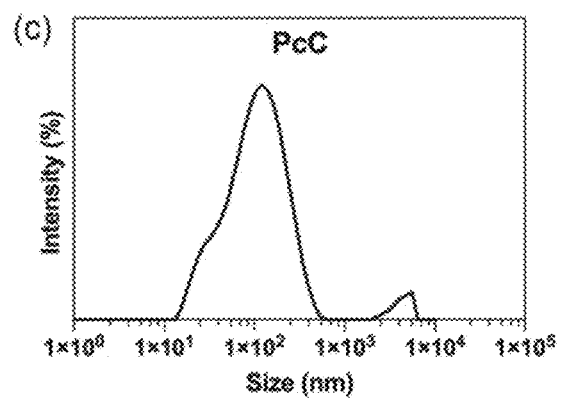
Figure 4D:
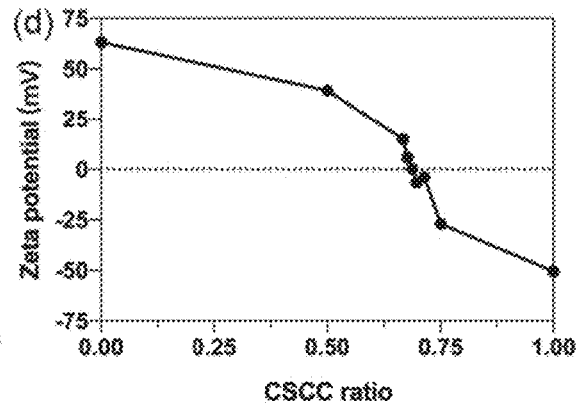

Dynamic light scattering (DLS)—CSCC and PEI-Chol (both at concentrations of 0.5 mg/mL) were mixed together at different volume ratios (CSCC:PEI-Chol=0:1, 1:1, 2:1, 2.1:1, 2.2:1, 2.3:1, 2.5:1, 3:1, 1:0) to make PcC suspensions. Particle sizes of PEI-Chol, CSCC and PcC suspension (CSCC:PEI-Chol=1:1), as well as zeta potential of PcC suspension were measured by DLS (Zetasizer Nano-S Malvern). In order to further study the electrostatic interactions between CSCC and PEI-Chol, DLS measurement for zeta potential detection was performed. Diluted PcC suspension was prepared by combining equal concentrations of CSCC and PEI-Chol at different volume ratios (FIG. 4D). A decrease in zeta potential from 63.2 mV to −50.4 mV was observed as CSCC volume ratio increased, and the PcC suspension became electrically neutral when CSCC:PEI-Chol (v/v) ratio reached around 2.2:1. According to the DLS results, the average particle size of PEI-Chol was approximately 105.2 nm (FIG. 4A), and the particle size of CSCC was approximately 219.8 nm (FIG. 4B). For PcC, some precipitation was detected as indicated by the DLS result (FIG. 4C). At very dilute concentrations, crosslinking precipitation occurred when PEI-Chol and CSCC were mixed.

Figures 5A, 5B:
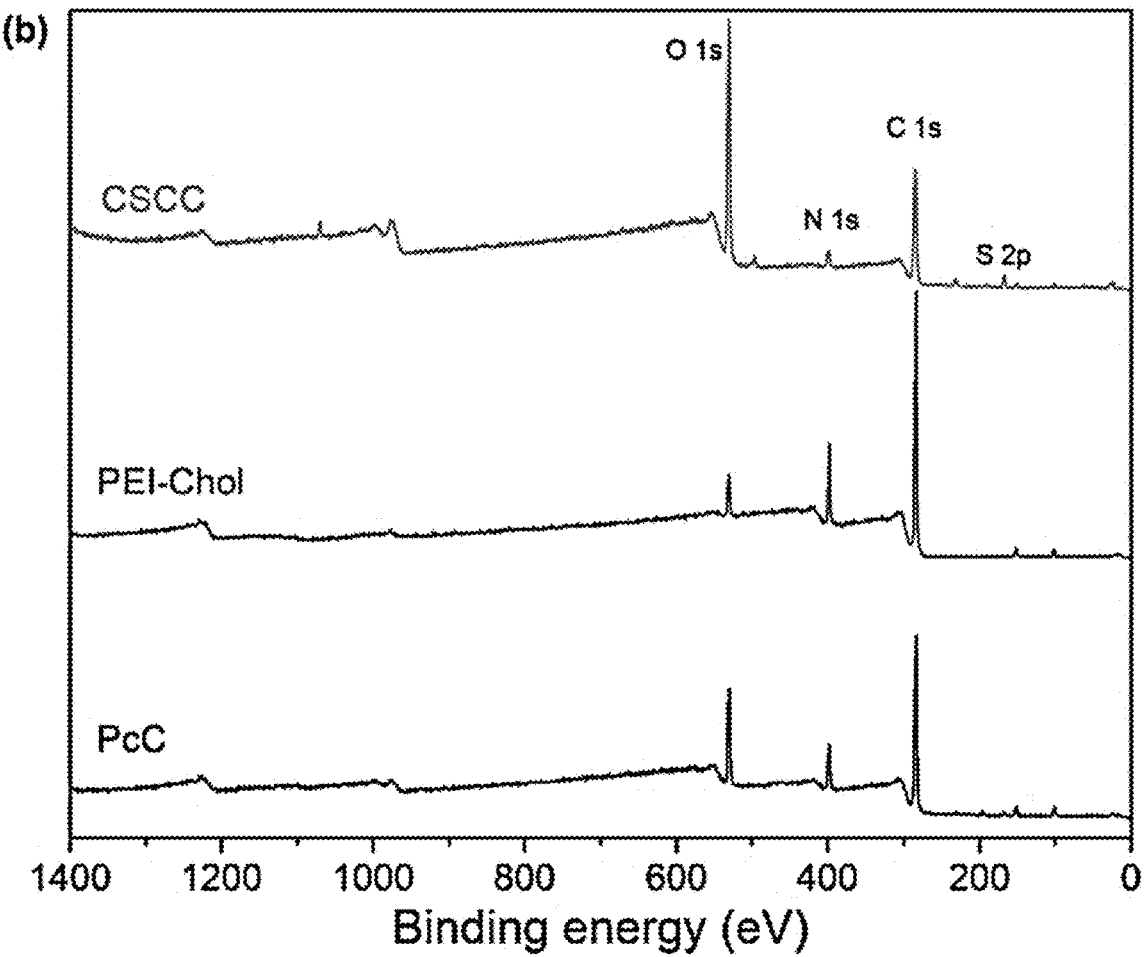
FIGS. 5A-5B.
Figure 6A:
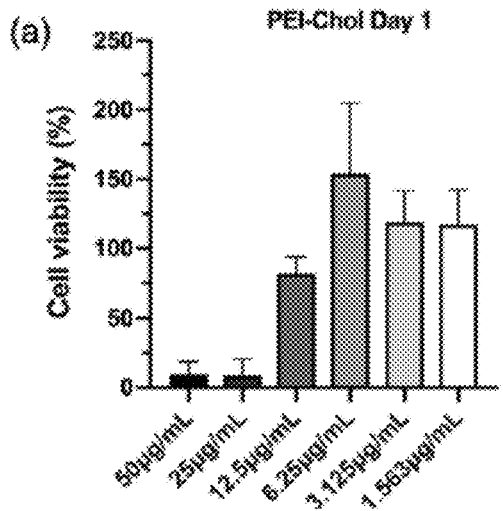
FIGS. 6A-6F. Graphs depicting cytotoxicity of different concentrations of PEI-Chol on day 1 (FIG. 6A), day 4 (FIG. 6B), and day 7 (FIG. 6C). Graphs depicting cytotoxicity of different concentrations of CSCC on day 1 (FIG. 6D), day 4 (FIG. 6E), and day 7 (FIG. 6F).
Figure 6D:
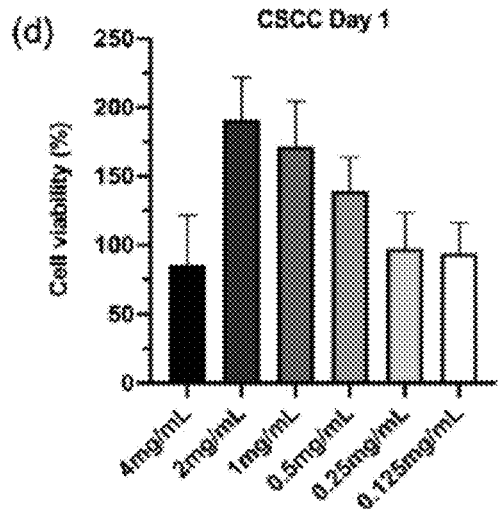
Figure 6B:
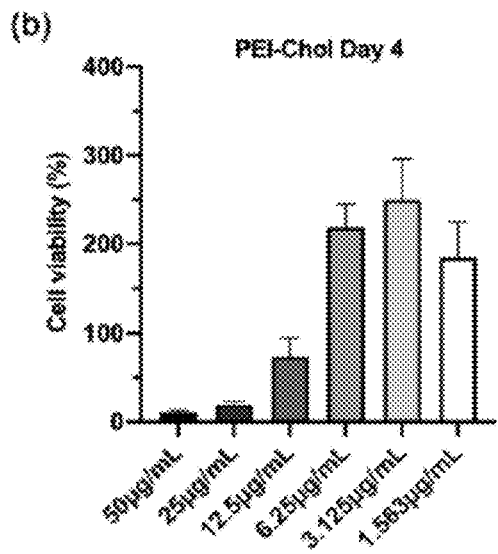
Figure 6E:
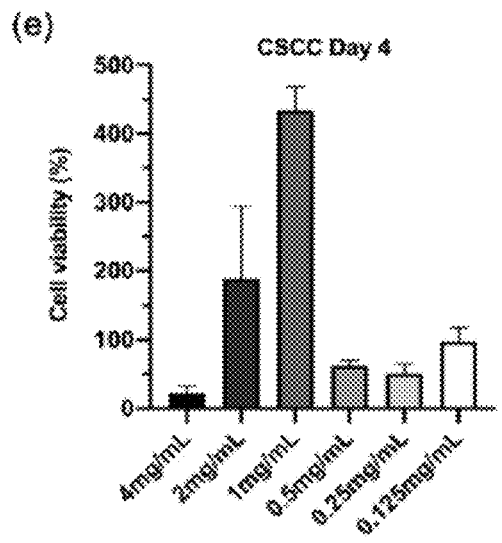
Figure 6C:
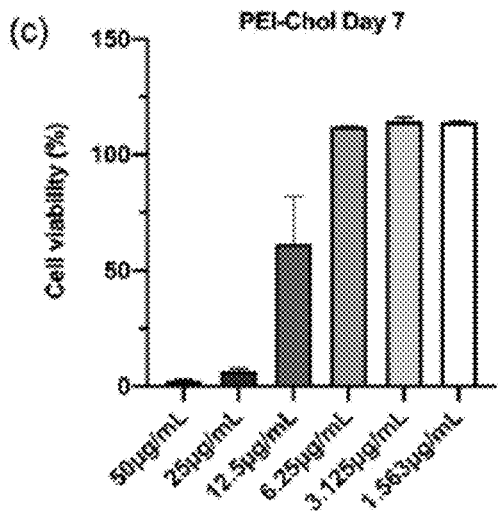
Figure 6F:
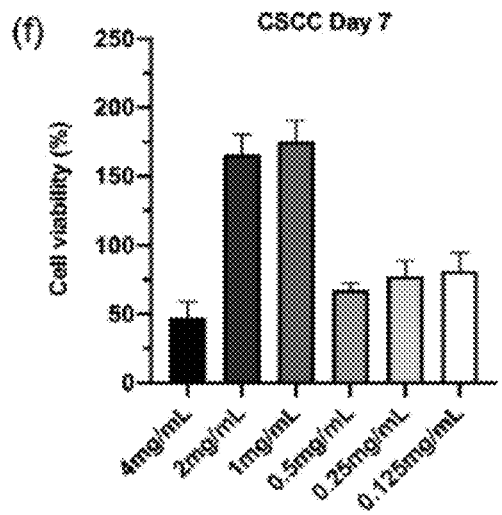

X-ray photoelectron spectroscopy (XPS)—Carbon (C), nitrogen (N), oxygen (O) and sulfur (S) were detected by XPS (PHI Model 5802) with a bandpass energy of 40 eV. PEI-Chol, CSCC and PcC were freeze-dried before detection. The X-ray photoelectron spectroscopy (XPS) analysis was performed to investigate the surface composition of CSCC, PEI-Chol, and their combination PcC (FIG. 5A and FIG. 5B). Four peaks with binding energies of 530.4, 399.2, 285.6, and 168.8 eV can be observed, representing the presence of O 1s, N 1s, C 1s and S 2p, respectively. Compared to undetectable sulfur content in PEI-Chol, PcC showed 0.8% sulfur on the material's surface, indicating the combination of these two polyelectrolytes. Based on the zeta potential measurement above, the PcC suspension became electrically neutral when CSCC:PEI-Chol (v/v) ration was approximately 2.2:1, which was the mass ratio of CSCC: PEI-Chol in each PcC bio-adhesive. The 0.8% S was less than the proportion calculated with the 2.2:1 mass ratio, indicating more Chol component was exposed to the surface of PcC bio-adhesive.

Not to be bound by theory, the adhesion may be attributed to a large extent to the catechol groups, while the cohesion may be derived from the electrostatic interaction and hydrophobic Chol. It is believed that PEI-Chol existed in water as micelles with hydrophilic PEI component exposed to the dispersion phase and hydrophobic Chol hidden inside. However, after contact with CSCC in aqueous solution, PEI-Chol may interact with CSCC through positive charges on PEI and negative charges on CS. Therefore, the balances of PEI-Chol aqueous solution and CSCC aqueous solution respectively may have been broken, resulting in exposure of Chol and CC. Due to the hydrophobicity of Chol, PcC may have been separated from the aqueous dispersion phase. At the same time, the PcC hydrogel may have been furnished with adhesion due to the exposed catechol groups on CC.

As demonstrated, the newly engineered PcC bio-adhesive can be fast and easily prepared for medical use. However, compared to dopamine based bio-adhesives, CC was relatively more stable during synthesis and improved the consistency of the CSCC products. Also, the catechol groups only oxidized or polymerized after addition of alkaline PEI-Chol, showing better stability for the reactant products that can improve storage life. Further, the PcC bio-adhesive was orange red in color, more pleasant than the black color of dopamine derived bio-adhesives.

Example 4

Internal adhesion, sealability, and acute toxicity of PcC bio-adhesive were determined.

Animal preparation and surgical procedures—In order to test the internal adhesion, sealability and acute toxicity of PcC bio-adhesive in vivo, rat seroma model and cartilage repair models were constructed. For rat mastectomy model, twelve female Sprague-Dawley® rats (SD rats), each weighting 200-300 g, were randomly divided into three groups, the saline control group (n=4), the PcC group (n=4), the TISSEEL® sealant (n=4). The experimental procedure is briefly described as follows. The animals were firstly anesthetized by isoflurane then placed in the supine position. The surgical area was shaved and disinfected with iodophor. Using scalpel and surgical scissors, a midline incision from cervical to glabella was made. The left ventral flap was lifted and separated from the muscle tissue to expose the pectoralis muscle, the axilla, the clavicle and the edges of the latissimus dorsi muscle. The pectoralis major and pectoralis minor muscles were removed using scissors. The inner surface of the lifted flap was then scraped 50 times with a scalpel to disrupt the lymphatic vessels. The wound was injected with 300 μL of saline, 300 μL of TISSEEL® kit, or PcC bio-adhesive, then the wound was closed with skin staples. The post-operative animals were monitored daily for wound dehiscence, infection, and the formation of seroma. On postoperative days 1, 4, and 7, seroma fluid was aspirated percutaneously through a syringe and the volume was measured. On postoperative day 7, all animals were euthanized by $CO_2$ asphyxiation. Subsequently, full-thickness biopsies of the skin and chest wall were collected, fixed, and embedded for histological analysis.

For the cartilage defect model, cylindrical defects with a diameter of 2 mm were created in the joint of SD rats. PcC/dLhCG and dLhCG were implanted into the defects on the left and right legs respectively, in order to eliminate individual differences. Nine duplicates for each group were used. The post-operative animals were monitored daily for wound dehiscence, infection, and the formation of lumps. At post-operative day 1, the rat was euthanized with $CO_2$ and the cartilage joints of both knees were collected. The tissues were paraffin-embedded after fixation and decalcification, and immunohistochemical (IHC) staining was performed on the sections.

Figure 8A:
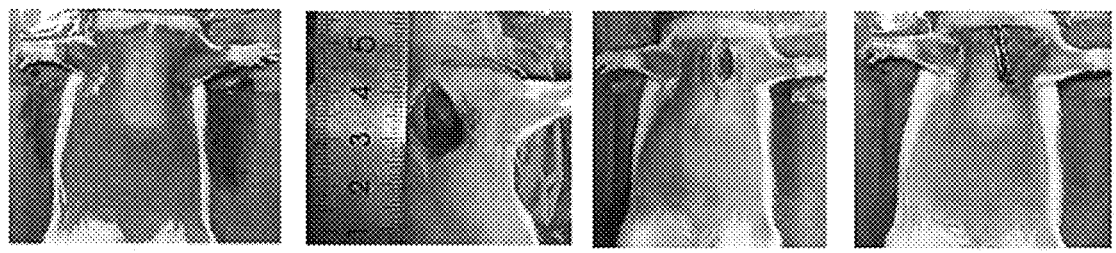
FIGS. 8A-8B.
Figure 8B:
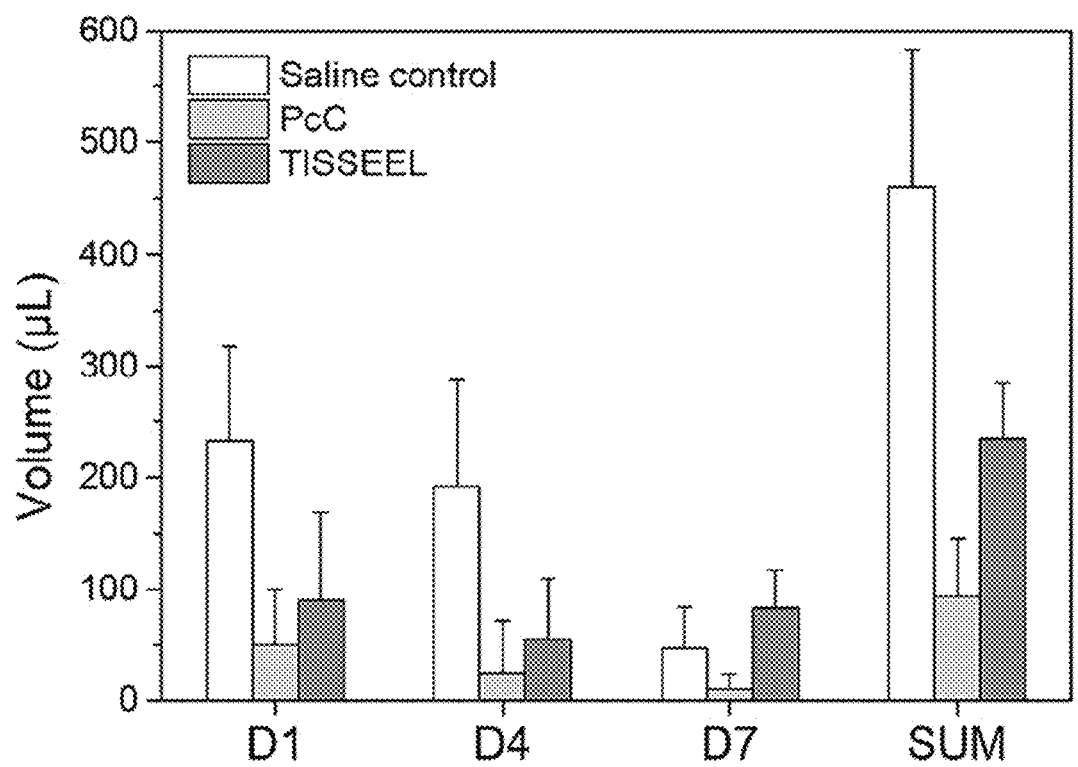

In vivo seroma prevention capability and biocompatibility evaluation—The process of rat mastectomy was illustrated in FIG. 8A. The post-operative rats showed no symptoms such as wound dehiscence, infection, or skin flap necrosis. The mean and total seroma volumes are depicted in FIG. 8B. In the saline control group, the mean seroma volume on days 1, 4, and 7 were 233.3±84.9 µL, 192.5±9 5.2 µL and 46.7±37.7 µL, respectively. As for the PcC group, the mean seroma volume on days 1, 4, and 7 were 50±49.6 µL, 25.0±47.1 µL and 10±14.1 µL, respectively. In the TISSEEL® group, the mean seroma volume on days 1, 4, and 7 were 90±78.7 µL, 55.0±54.9 µL and 83.3±33.9 µL, respectively. The total seroma volume of these three groups were 472.5±123.0 µL, 85±52.5 µL and 228.3±4 9.5 µL, respectively. The PcC group produced the least total seroma volume within one week after surgery. On day 7, the seroma volume was almost zero, whereas the TISSEEL® group seroma volume was elevated.

Figure 9:
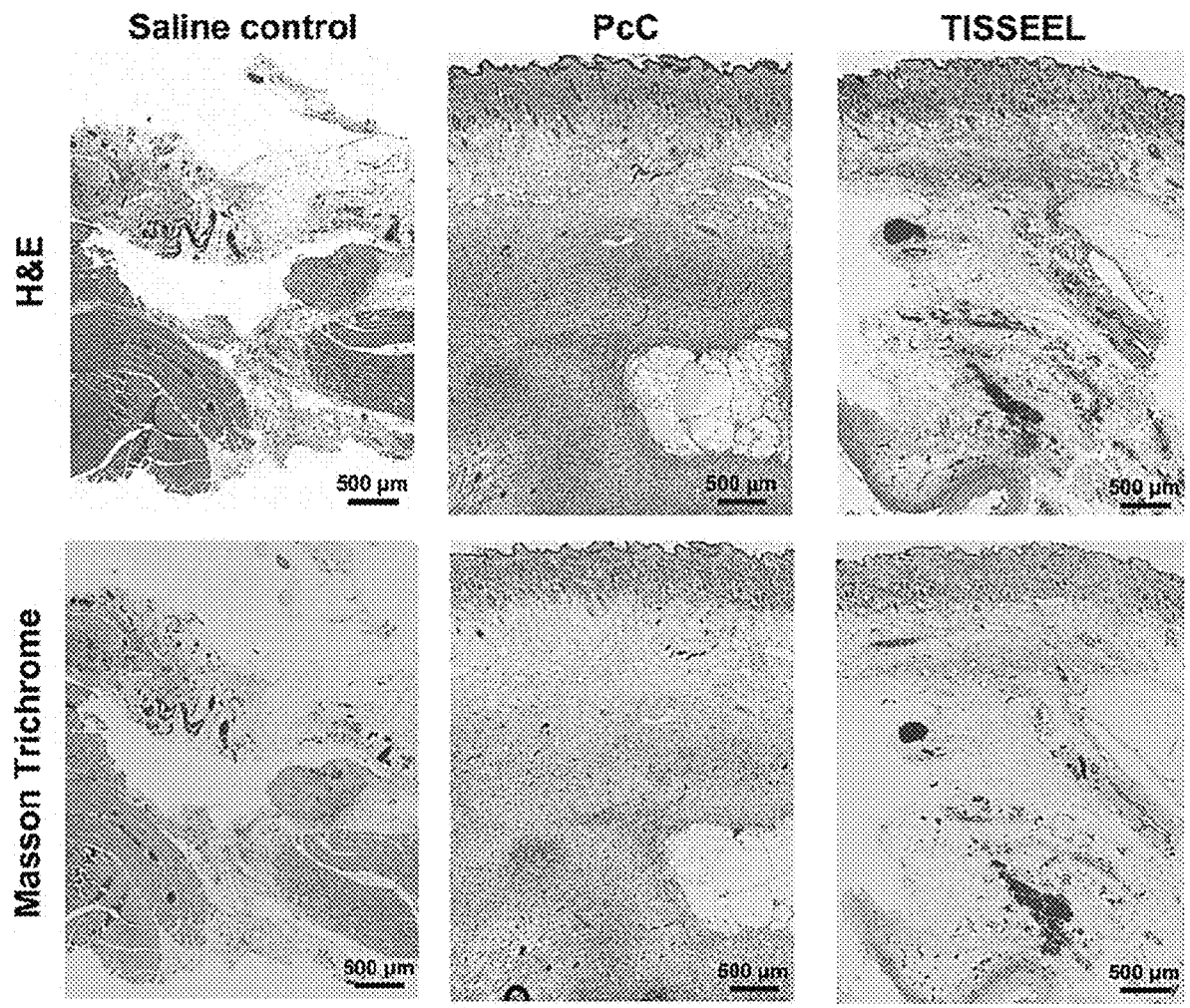
FIG. 9 is a series of images of histopathological evaluation of H&E and Masson Trichrome staining.
Figure 10A:
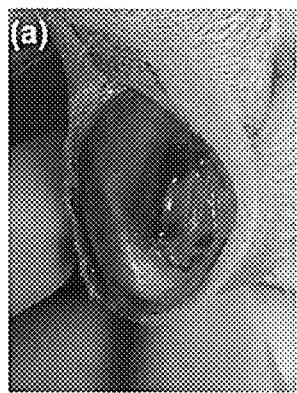
FIGS. 10A-10D.
Figure 10B:
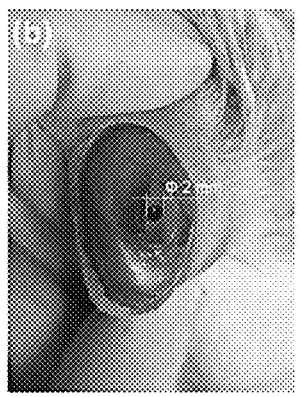
Figure 10C:
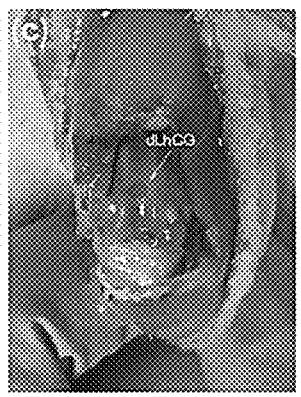
Figure 10D:
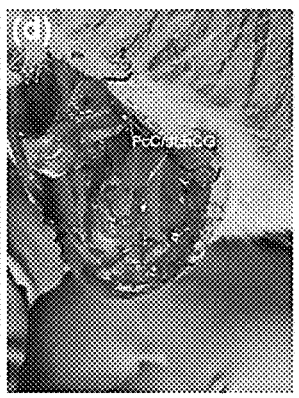

As shown in FIG. 9, Histological evaluation of the resected area showed that the skin flap was completely separated from the chest wall and formed a dead cavity in the control saline group. By contrast, in the PcC and TISSEEL® group, the skin flap was firmly adhered to the chest wall without gaps.

Photos of SD rats' cartilage joint implanted with dLhCG and PcC-coated dLhCG on day 1 are shown in FIG. 10A through FIG. 10D. No lump, infection, or inflammation was found, indicating there was no hyperacute rejection.

Figure 11:
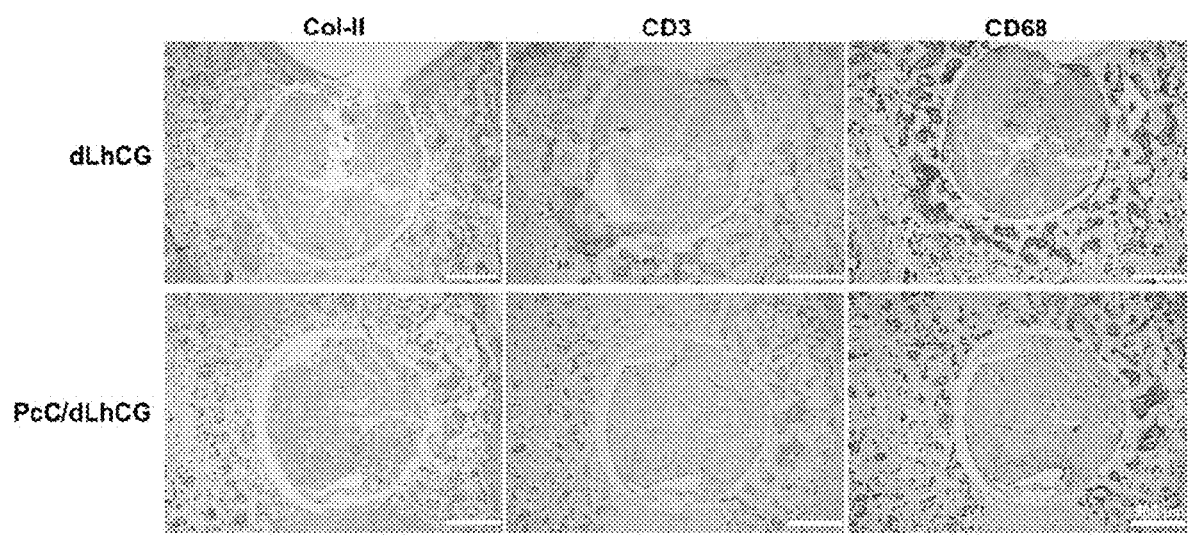
FIG. 11 is a series of images of IHC staining of Col-II, CD3, and CD68 of dLhCG, and PcC/dLhCG on day 1.

IHC staining of collage type II (Col-II), macrophages (CD68) and T cells (CD3) were conducted for further study. As shown in FIG. 11, both dLhCG and PcC/dLhCG showed positive Col-II, indicating that the coating of PcC bioadhesive did not affect the collagen phenotype of dLhCG. IHC staining showed mild immune and inflammatory responses after the graft implantation. Macrophages (CD68) and T cells (CD3) were stained in dark brown and primarily present on graft surfaces. Notably, CD68 presented significantly darker and larger staining on both the surface and interior of dLhCG, suggesting that macrophage inflammation was much more severe in dLhCG than in the PcC/dLhCG. Similarly, T cells (CD3) staining of dLhCG was darker brown compared to PcC-coated dLhCG, with only a few T cells (CD3) distributed on the PcC/dLhCG surface and almost none inside. The day 1 IHC staining results demonstrated that PcC bio-adhesive does not cause immune rejection, demonstrating the biocompatibility of the PcC bio-adhesive.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

1. Chen, X.; Yuk, H.; Wu, J.; Nabzdyk, C. S.; Zhao, X., Instant tough bioadhesive with triggerable benign detachment. Proceedings of the National Academy of Sciences 2020, 117 (27), 15497-15503.
2. Zhang, L.; Liu, M.; Zhang, Y.; Pei, R., Recent progress of highly adhesive hydrogels as wound dressings. Biomacromolecules 2020, 21 (10), 3966-3983.
3. Li, J.; Yu, X.; Martinez, E. E.; Zhu, J.; Wang, T.; Shi, S.; Shin, S. R.; Hassan, S.; Guo, C., Emerging Biopolymer—Based Bioadhesives. Macromolecular Bioscience 2022, 22 (2), 2100340.
4. Duan, W.; Bian, X.; Bu, Y., Applications of bioadhesives: a mini review. Frontiers in Bioengineering and Biotechnology 2021, 9.
5. Mehdizadeh, M.; Yang, J., Design strategies and applications of tissue bioadhesives. Macromolecular bioscience 2013, 13 (3), 271-288.
6. Hino, M.; Ishiko, O.; Honda, K. i.; Yamane, T.; Ohta, K.; Takubo, T.; Tatsumi, N., Transmission of symptomatic parvovirus B19 infection by fibrin sealant used during surgery. British journal of haematology 2000, 108 (1), 194-195.
7. Horowitz, B.; Busch, M., Estimating the pathogen safety of manufactured human plasma products: application to fibrin sealants and to thrombin. Transfusion 2008, 48 (8), 1739-1753.
8. Ma, C.; Sun, J.; Li, B.; Feng, Y.; Sun, Y.; Xiang, L.; Wu, B.; Xiao, L.; Liu, B.; Petrovskii, V. S., Ultra-strong bio-glue from genetically engineered polypeptides. Nature communications 2021, 12 (1), 1-14.
9. Ge, L.; Chen, S., Recent advances in tissue adhesives for clinical medicine. Polymers 2020, 12 (4), 939.
10. Farrar, D. F., Bone adhesives for trauma surgery: A review of challenges and developments. International journal of adhesion and adhesives 2012, 33, 89-97.
11. Cedano Serrano, F.; Pinzón, L.; Narváez, D.; Castro Paéz, C.; Moreno-Serrano, C.; Tabima, D.; Salcedo, F.; Briceno, J.; Casas-Rodriguez, J., Evaluation of a water-resistant and biocompatible adhesive with potential use in bone fractures. Journal of adhesion science and Technology 2017, 31 (13), 1480-1495.
12. Yuk, H.; Varela, C. E.; Nabzdyk, C. S.; Mao, X.; Padera, R. F.; Roche, E. T.; Zhao, X., Dry double-sided tape for adhesion of wet tissues and devices. Nature 2019, 575 (7781), 169-174.
13. Farzaneh, H.; Nik, M. E.; Mashreghi, M.; Saberi, Z.; Jaafari, M. R.; Teymouri, M., A study on the role of cholesterol and phosphatidylcholine in various features of liposomal doxorubicin: from liposomal preparation to therapy. International journal of pharmaceutics 2018, 551 (1-2), 300-308.
14. Gruber, A.; Joshi, A. A.; Graff, P.; Cuellar-Camacho, J. L.; Hedtrich, S.; Klinger, D., Influence of Nanogel Amphiphilicity on Dermal Delivery: Balancing Surface Hydrophobicity and Network Rigidity. Biomacromolecules 2021, 23 (1), 112-127.
15. Zhu, W.; Iqbal, J.; Wang, D.-A., A DOPA-functionalized chondroitin sulfatebased adhesive hydrogel as a promising multi-functional bioadhesive. Journal of Materials Chemistry B 2019, 7 (10), 1741-1752.
16. Tao, C.; Jin, M.; Yao, H.; Wang, D.-A., Dopamine based adhesive nanocoatings on extracellular matrix (ECM) based grafts for enhanced host-graft interfacing affinity. Nanoscale 2021, 13 (43), 18148-18159.
17. Jin, M.; Shi, J.; Zhu, W.; Yao, H.; Wang, D.-A., Polysaccharide-based biomaterials in tissue engineering: a review. Tissue Engineering Part B: Reviews 2021, 27 (6), 604-626.
18. Wang, D.-a.; Narang, A. S.; Kotb, M.; Gaber, A. O.; Miller, D. D.; Kim, S. W.; Mahato, R. I., Novel branched poly (Ethylenimine)-cholesterol water-soluble lipopolymers for gene delivery. Biomacromolecules 2002, 3 (6), 1197-1207.
19. Ren, J.; Kong, R.; Gao, Y.; Zhang, L.; Zhu, J., Bioinspired adhesive coatings from polyethylenimine and tannic acid complexes exhibiting antifogging, self-cleaning, and antibacterial capabilities. Journal of Colloid and Interface Science 2021, 602, 406-414.
20. Cui, Y.; Yin, L.; Sun, X.; Zhang, N.; Gao, N.; Zhu, G., A Universal and Reversible Wet Adhesive via Straightforward Aqueous Self-Assembly of Polyethylenimine and Polyoxometalate. ACS Applied Materials & Interfaces 2021, 13 (39), 47155-47162.
21. Moulay, S., Dopa/catechol-tethered polymers: Bioadhesives and biomimetic adhesive materials. Polymer Reviews 2014, 54 (3), 436-513.
22. Guyot, C.; Cerruti, M.; Lerouge, S., Injectable, strong and bioadhesive catecholchitosan hydrogels physically crosslinked using sodium bicarbonate. Materials Science and Engineering: C 2021, 118, 111529.
23. Shi, C.; Chen, X.; Zhang, Z.; Chen, Q.; Shi, D.; Kaneko, D., Mussel inspired bio-adhesive with multi-interactions for tissue repair. Journal of Biomaterials Science, Polymer Edition 2020, 31 (4), 491-503.
24. Zhu, W.; Peck, Y.; Iqbal, J.; Wang, D.-A., A novel DOPA-albumin based tissue adhesive for internal medical applications. Biomaterials 2017, 147, 99-115.
25. Fan, C.; Fu, J.; Zhu, W.; Wang, D.-A., A mussel-inspired double-crosslinked tissue adhesive intended for internal medical use. Acta biomaterialia 2016, 33, 51-63.
26. He, J.; Xu, L.; Le Yang, X. W., Epigallocatechin gallate is the most effective catechin against antioxidant stress via hydrogen peroxide and radical scavenging activity. Medical Science Monitor: International Medical Journal of Experimental and Clinical Research 2018, 24, 8198.
27. Pheomphun, P.; Treesubsuntorn, C.; Thiravetyan, P., Effect of exogenous catechin on alleviating O3 stress: the role of catechin-quinone in lipid peroxidation, salicylic acid, chlorophyll content, and antioxidant enzymes of Zamioculcas zamiifolia. Ecotoxicology and environmental safety 2019, 180, 374-383.
28. Spizzirri, U. G.; Parisi, O. I.; Iemma, F.; Cirillo, G.; Puoci, F.; Curcio, M.; Picci, N., Antioxidant-polysaccharide conjugates for food application by eco-friendly grafting procedure. Carbohydrate Polymers 2010, 79 (2), 333-340.
29. Nie, X.; Chuah, Y. J.; Zhu, W.; He, P.; Peck, Y.; Wang, D.-A., Decellularized tissue engineered hyaline cartilage graft for articular cartilage repair. Biomaterials 2020, 235, 119821.
30. Zhu, W.; Yang, J.; Iqbal, J.; Peck, Y.; Fan, C.; Wang, D.-A., A musselinspired double-crosslinked tissue adhesive on rat mastectomy model: seroma prevention and in vivo biocompatibility. Journal of Surgical Research 2017, 215, 173-182.
31. Choi, M. S.; Kim, H. K.; Kim, W. S.; Bae, T. H.; Kim, M. K., A comparison of triamcinolone acetonide and fibrin glue for seroma prevention in a rat mastectomy model. Annals of plastic surgery 2012, 69 (2), 209-212.

What is claimed is:

1. A bio-adhesive comprising a polyanionic polymer and a polycationic polymer functionalized with a hydrophobic moiety, wherein the functionalized polycationic polymer comprises a polycationic polymer having a hydrophobic moiety, wherein the bio-adhesive comprises:
   from 15 to 60% by weight, based on a total weight of the bio-adhesive, of the functionalized polycationic polymer;
   from 40 to 85% by weight, based on a total weight of the bio-adhesive, of the polyanionic polymer; or
   from 15 to 60% by weight, based on a total weight of the bio-adhesive, of the functionalized polycationic polymer and from 40 to 85% by weight, based on a total weight of the bio-adhesive, of the polyanionic polymer.

2. The bio-adhesive of claim 1, wherein the functionalized polycationic polymer comprises one or a combination of polyethyleneimine, chitosan, poly dimethyl diallyl ammonium chloride, and polyamidoamine-epichlorohydrin.

3. The bio-adhesive of claim 1, wherein the hydrophobic moiety comprises one or a combination of a cholesterol, stearic acid, oleic acid, lecithin, sulfonate, [or] and a quaternary ammonium salt moiety.

4. The bio-adhesive of claim 1, wherein the polyanionic polymer comprises a negatively-charged polysaccharide.

5. The bio-adhesive of claim 4, wherein the negatively-charged polysaccharide comprises one or a combination of chondroitin sulfate, glycosaminoglycan, carrageenan, gum Arabic, alginate, xanthan, guar gum, pectin, sodium alginate, hyaluronic acid, gellan gum, and heparin.

6. The bio-adhesive of claim 1, wherein the polyanionic polymer further comprises at least one phenolic moiety.

7. The bio-adhesive of claim 6, wherein the phenolic moiety is selected from catechol, catechin, dopamine, levopamine, epicatechin, or a combination thereof.

8. A medical adhesive kit for adhering biological tissues comprising the bio-adhesive of claim 1.

9. A method for preparing a bio-adhesive of claim 1, the method comprising contacting a polycationic polymer comprising at least one hydrophobic moiety with a polyanionic polymer comprising at least one phenolic moiety to obtain the bio-adhesive.

10. The method of claim 9, wherein the polycationic polymer comprises polyethyleneimine, chitosan, diallyl ammonium chloride, polyamidoamine-epichlorohydrin, or a combination thereof.

11. The method of claim 9, wherein the hydrophobic moiety comprises a cholesterol, stearic acid, oleic acid, lecithin, sulfonate, or a quaternary ammonium salt moiety, or a combination thereof.

12. The method of claim 9, wherein the polyanionic polymer comprises a negatively-charged polysaccharide comprising chondroitin sulfate, glycosaminoglycan, carrageenan, gum Arabic, alginate, xanthan, guar gum, pectin, sodium alginate, hyaluronic acid, gellan gum, heparin, or a combination thereof.

13. The method of claim 9, wherein the phenolic moiety comprises catechol, catechin, dopamine, levopamine, epicatechin, or a combination thereof.

14. A method for adhering two surfaces, the method comprising contacting the bio-adhesive of claim 1 to a first surface to form a bio-adhesive coated surface and contacting the bio-adhesive coated surface with a second surface, wherein contacting the bio-adhesive coated surface with a second surface adheres the first and second surfaces.

15. The method of claim 14, wherein the first and/or second surface is a surface of a biological material.

16. The method of claim 14, wherein the first and/or second surface is a surface of a cartilage, bone, shell, claw, tooth, or nail.

17. The method of claim 14, wherein the first surface is wet when contacted with the bio-adhesive and/or the second surface is wet when contacted with the bio-adhesive coated surface.

18. The method of claim 14, wherein the method further comprises contacting the adhered first and second surface with water.

* * * * *

UNITED STATES PATENT AND TRADEMARK OFFICE
CERTIFICATE OF CORRECTION

PATENT NO. : 12,233,182 B2
APPLICATION NO. : 17/959091
DATED : February 25, 2025
INVENTOR(S) : Dong-An Wang et al.

It is certified that error appears in the above-identified patent and that said Letters Patent is hereby corrected as shown below:

In the Specification

At Column 17, Line number 6, delete "(FIG. 1*i*)" and replace with --(FIG. 1B)--.
At Column 17, Line number 48, delete "6.25 g/mL" and replace with --6.25 µg/mL--.
At Column 18, Line number 14, delete "µ2x5x30" and replace with --2x5x30--.
At Column 19, Line number 26, delete "5 L" and replace with --5 µL--.
At Column 19, Line number 33, delete "50.280±6.720" and replace with --50.28°±6.72°--.
At Column 19, Line number 34, delete "(15.77°+5.67°)" and replace with --(15.77°±5.67°)--.
At Column 19, Line number 34, delete "(26.08°+5.98°)" and replace with --(26.08°±5.98°)--.

In the Claims

At Column 24, Claim number 3, Line number 39, delete "[or]".

Signed and Sealed this
Fifteenth Day of April, 2025

Coke Morgan Stewart
*Acting Director of the United States Patent and Trademark Office*